US008772036B2

(12) United States Patent
Frank et al.

(10) Patent No.: US 8,772,036 B2
(45) Date of Patent: Jul. 8, 2014

(54) AUTOMATED METHOD FOR SAMPLE DISTRIBUTION AND ISOLATION OF AN ANALYTE WITH A SOLID SUPPORT

(75) Inventors: Paul Frank, Ennetbuergen (CH); Andreas Gisler, Thalwil (CH); Robert Huesler, Root (CH); Rolf Knobel, Rotkreuz (CH); Siegfried Mueller, Meierskappel (CH); Urs Schnieper, Adligenswil (CH); Heinz Trueeb, Hochdorf (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 488 days.

(21) Appl. No.: 13/169,559

(22) Filed: Jun. 27, 2011

(65) Prior Publication Data

US 2012/0164735 A1    Jun. 28, 2012

(30) Foreign Application Priority Data

Jun. 29, 2010   (EP) ..................................... 10167647

(51) Int. Cl.
*G01N 35/10* (2006.01)
*G01N 1/10* (2006.01)

(52) U.S. Cl.
USPC ................. 436/43; 422/63; 422/67; 422/509; 422/510; 422/511; 422/514; 422/515; 422/516; 436/49; 436/54; 436/180

(58) Field of Classification Search
USPC ........ 422/63, 67, 509–511, 514–516; 436/43, 436/49, 54, 180
See application file for complete search history.

(56) References Cited

U.S. PATENT DOCUMENTS

| | | | | |
|---|---|---|---|---|
| 3,581,575 | A | * | 6/1971 | Butler .......................... 73/864.12 |
| 4,734,261 | A | * | 3/1988 | Koizumi et al. ............... 422/516 |
| 5,306,510 | A | * | 4/1994 | Meltzer ........................... 422/65 |
| 5,335,481 | A | * | 8/1994 | Ward ............................... 53/446 |
| 5,482,863 | A | * | 1/1996 | Knobel ........................... 436/54 |
| 5,647,994 | A | * | 7/1997 | Tuunanen et al. ............. 210/695 |
| 5,660,792 | A | * | 8/1997 | Koike ............................. 422/63 |
| 5,702,950 | A | * | 12/1997 | Tajima ........................... 436/49 |
| 6,187,270 | B1 | * | 2/2001 | Schmitt et al. ................ 422/527 |
| 6,235,244 | B1 | * | 5/2001 | Allen et al. ................... 422/525 |
| 6,358,470 | B1 | * | 3/2002 | Higuchi .......................... 422/63 |
| 6,451,263 | B1 | * | 9/2002 | Sarrine ....................... 73/863.32 |
| 8,128,892 | B2 | * | 3/2012 | Butz et al. ..................... 422/501 |
| 2002/0106804 | A1 | * | 8/2002 | Tanaka ............................ 436/54 |
| 2002/0117013 | A1 | * | 8/2002 | Bem ........................... 73/864.25 |
| 2004/0096360 | A1 | | 5/2004 | Toi et al. |
| 2004/0161368 | A1 | | 8/2004 | Holtlund et al. |
| 2006/0081539 | A1 | | 4/2006 | Safar et al. |
| 2010/0137574 | A1 | | 6/2010 | Bachmann |

FOREIGN PATENT DOCUMENTS

| | | |
|---|---|---|
| DE | 3805808 A1 | 9/1989 |
| EP | 0965842 A1 | 12/1999 |
| EP | 2156891 A2 | 2/2010 |
| EP | 0965842 B1 | 3/2010 |

(Continued)

*Primary Examiner* — Arlen Soderquist
(74) *Attorney, Agent, or Firm* — David J. Chang; M. Reza Savari

(57) ABSTRACT

A method is described for distributing samples within an automated analyzer from a linear arrangement of sample vessels to a processing plate in a two-dimensional n×m arrangement wherein samples are sorted, followed by transfer with a pipetting device with a linear arrangement to a processing vessel in a two-dimensional n×m arrangement and subsequent processing of samples using a second pipetting device which has a two-dimensional n×m arrangement.

7 Claims, 19 Drawing Sheets

(56) References Cited

FOREIGN PATENT DOCUMENTS

| | | | |
|---|---|---|---|
| EP | 1712285 | B1 | 6/2011 |
| GB | 2425498 | A | 11/2006 |
| JP | 08211071 | A | 8/1996 |
| JP | 03652424 | B2 | 5/2005 |
| WO | 02059626 | A1 | 8/2002 |
| WO | 2005009202 | A2 | 2/2005 |

* cited by examiner

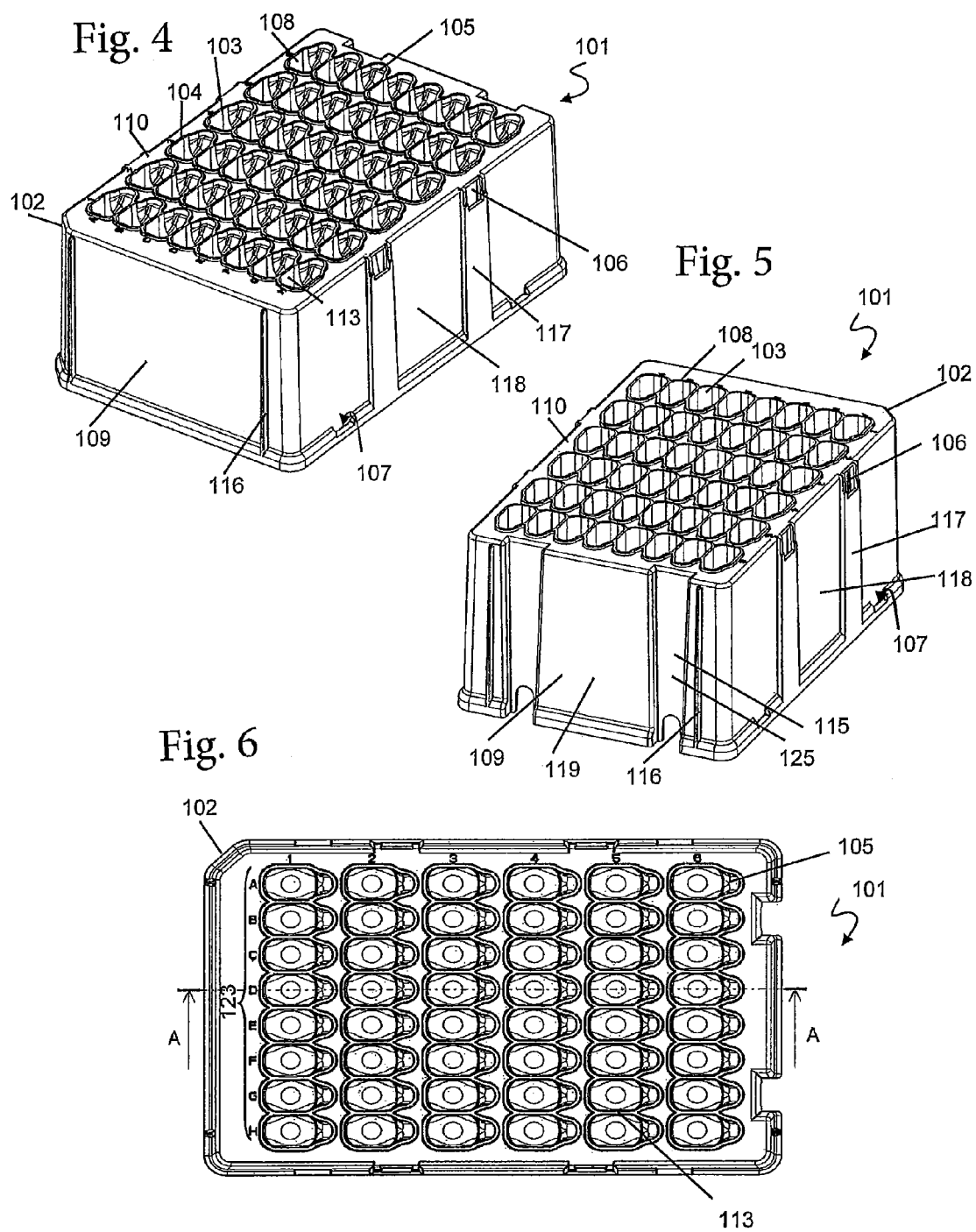

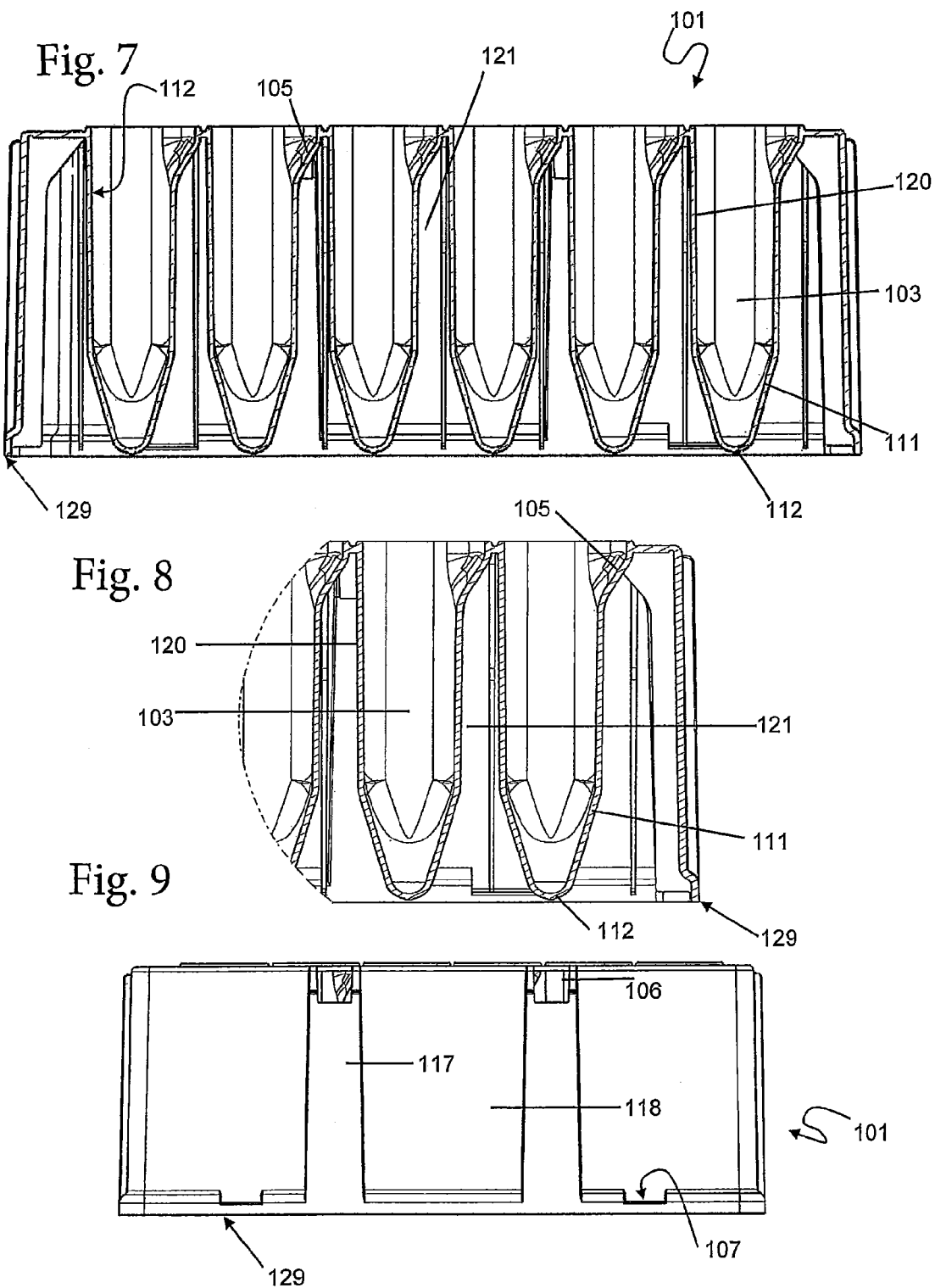

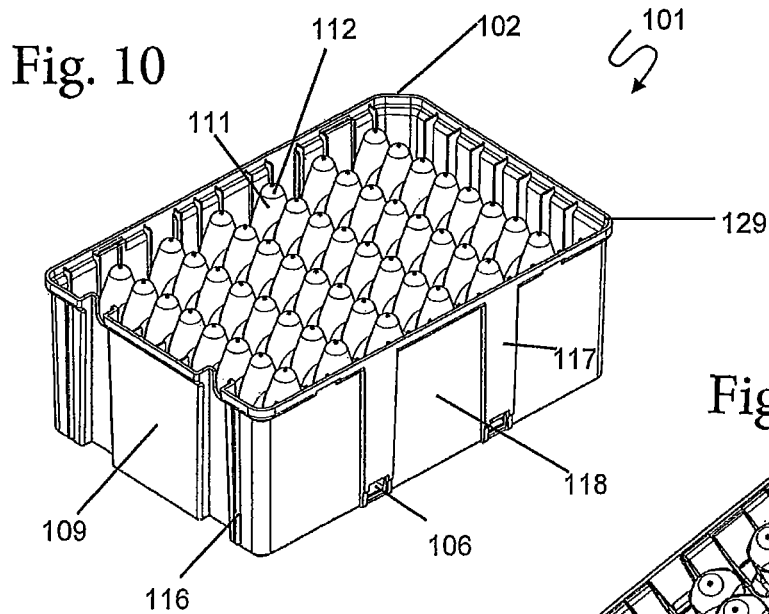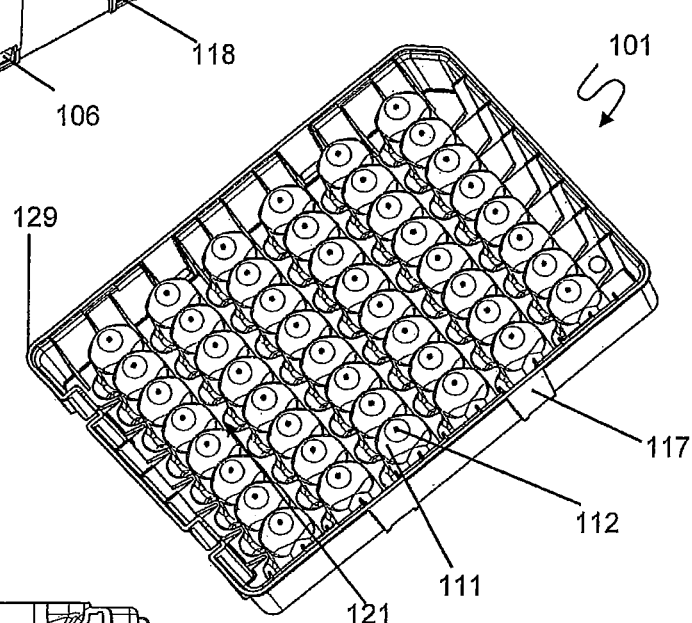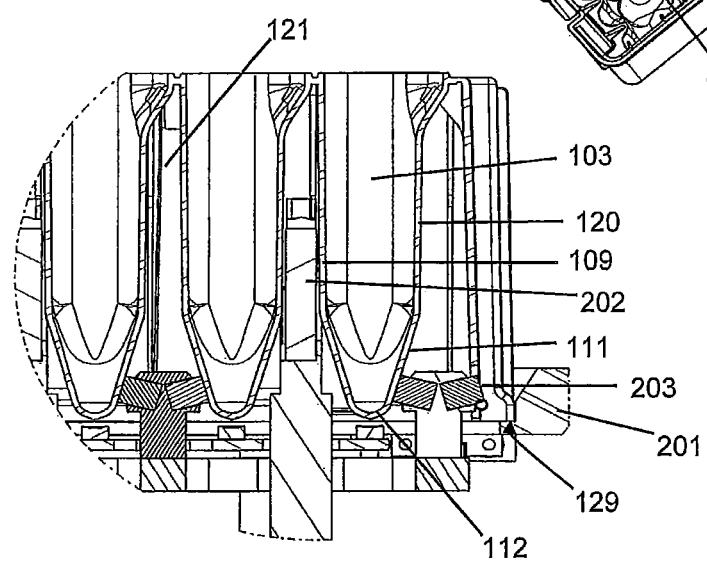

Fig. 18
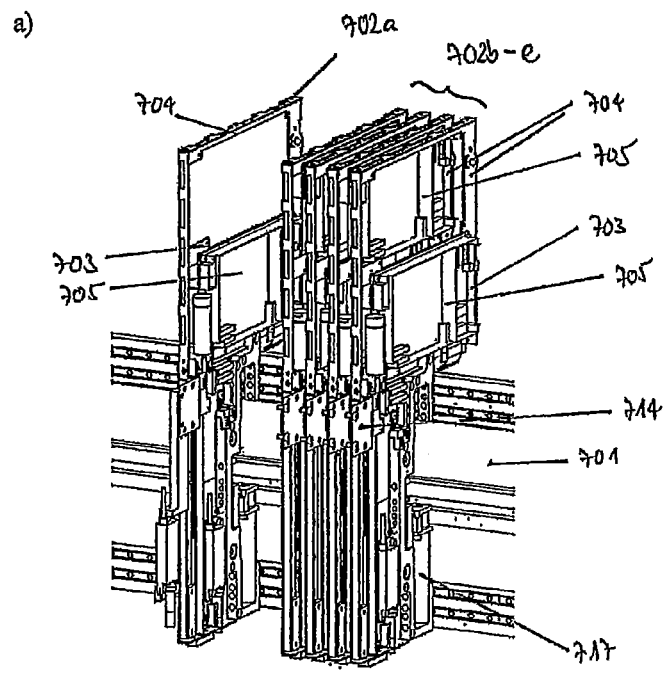
a)
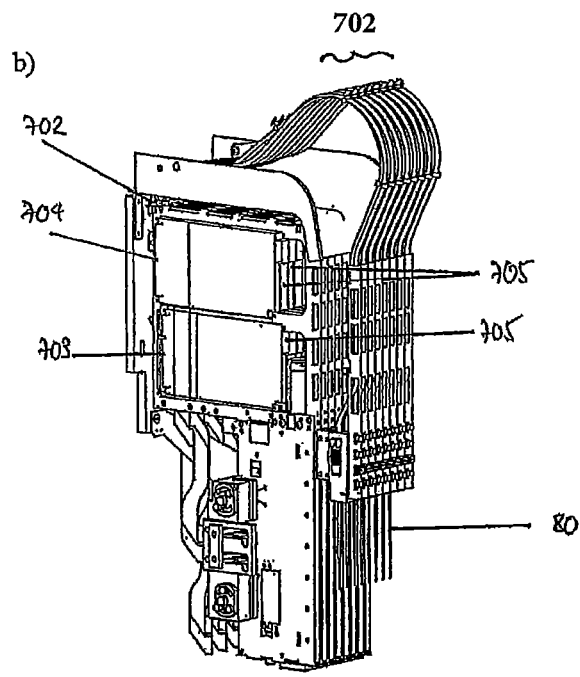
b)

Fig. 20
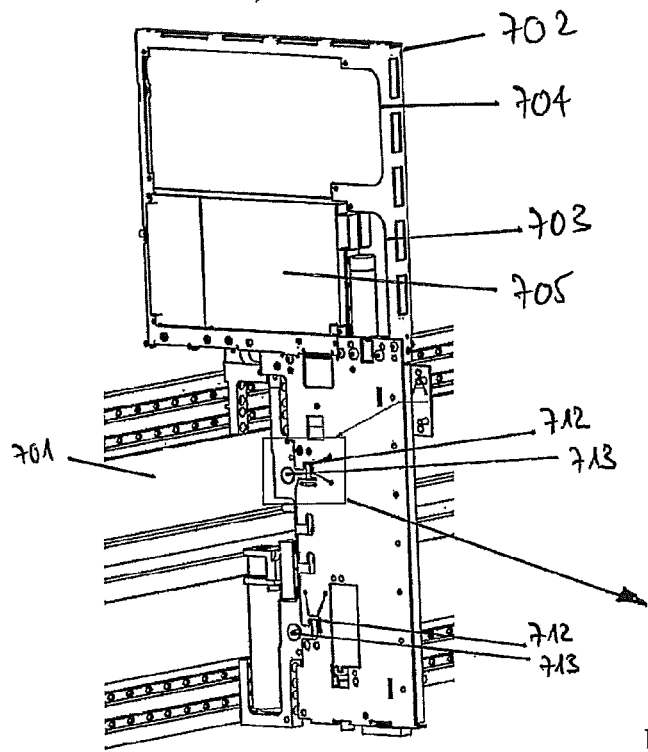
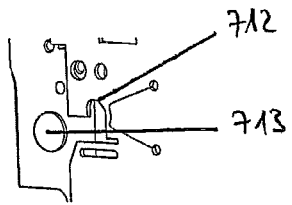
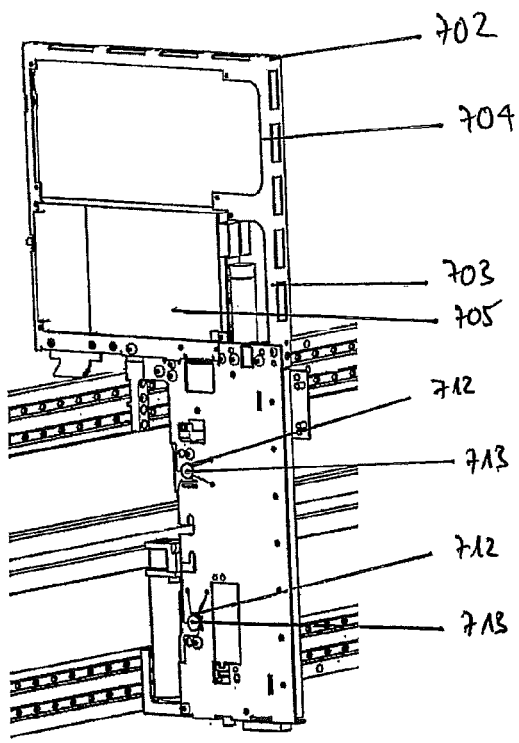

Fig. 22    a)
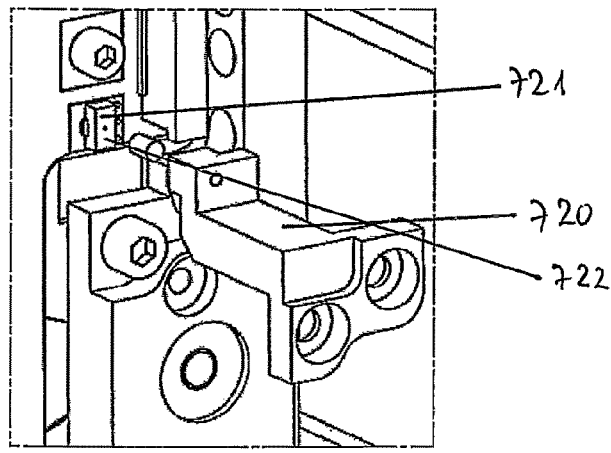
b)
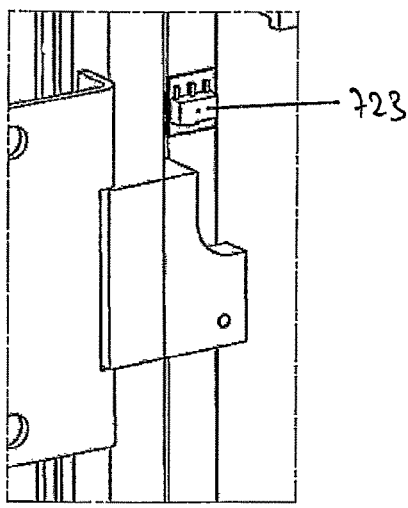
c)
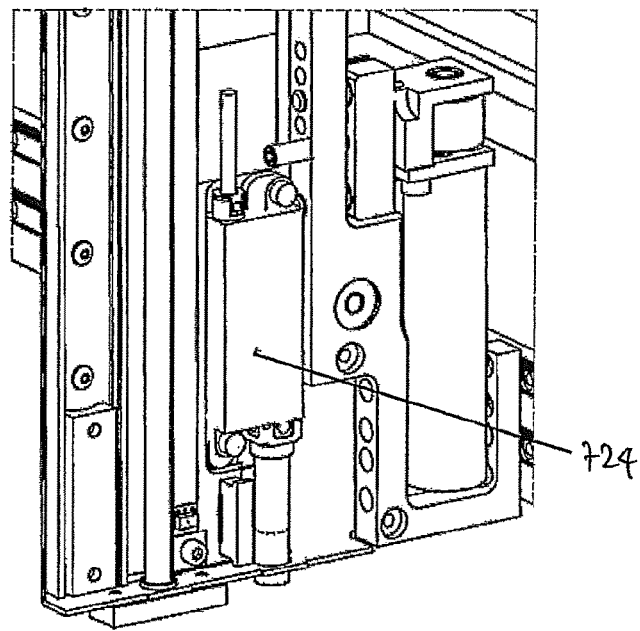

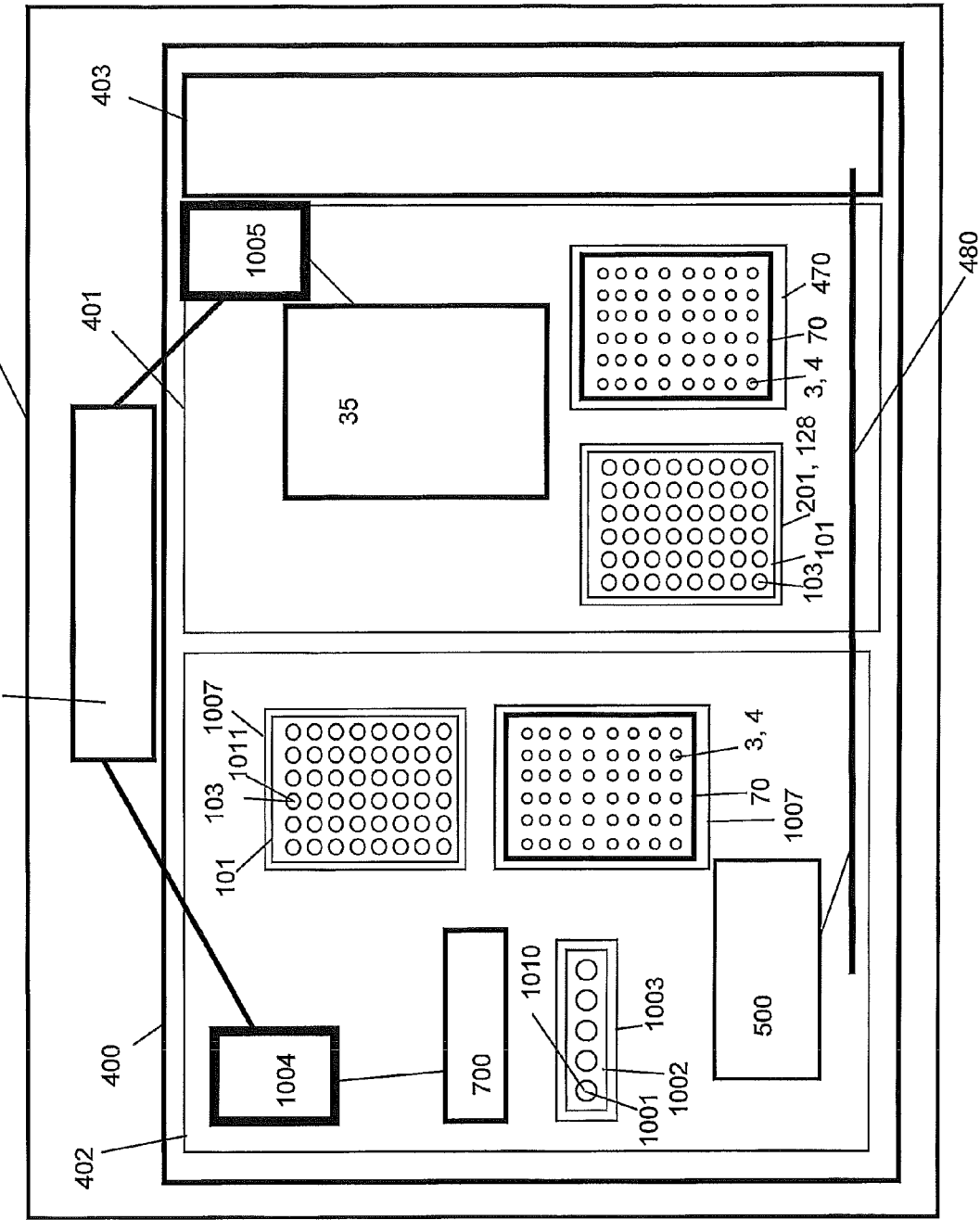

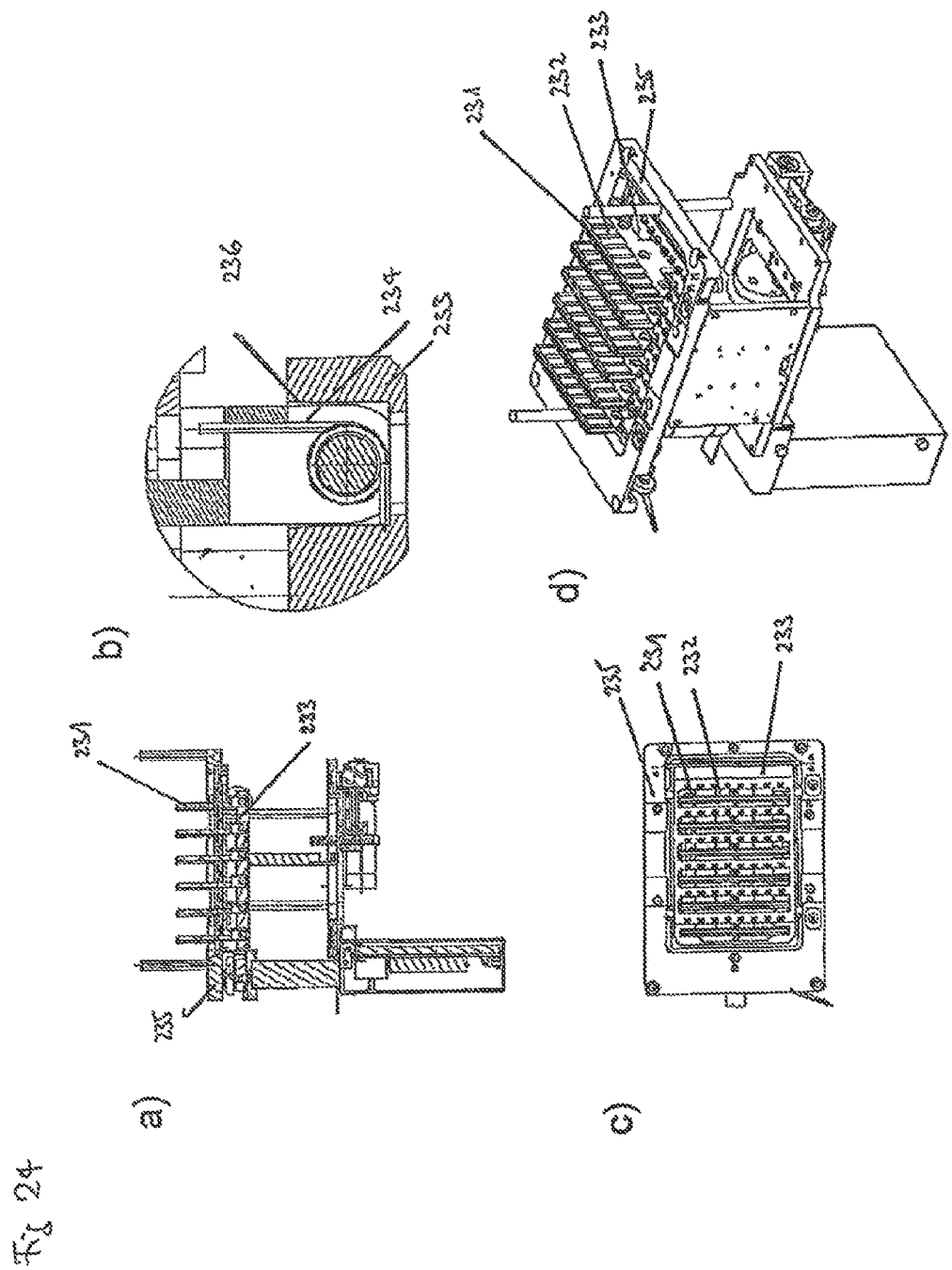

AUTOMATED METHOD FOR SAMPLE DISTRIBUTION AND ISOLATION OF AN ANALYTE WITH A SOLID SUPPORT

CROSS-REFERENCES TO RELATED APPLICATIONS

The present application claims the benefit of priority under 35 U.S.C. §119 of EP10167647.6, filed Jun. 29, 2010, the contents of which is incorporated by reference herein in its entirety.

FIELD OF THE INVENTION

The present invention relates to a method for isolating analytes in an automated system, and to an analytical system for processing an analyte.

BACKGROUND OF THE INVENTION

Analytical systems used in the field of diagnostics require processing of samples comprising analytes to be analyzed.

Such processing involves sorting of samples, transfer of vessels, or of liquid samples and reagents from one vessel to another. For higher throughput, simultaneous processing is often performed using multiple consumables, such as pipette tips and single vessels or multiwell plates. There is also interest in analyzers which are fully integrated and which carry out all steps necessary from sample preparation to the obtaining of the results of the analytical method. One such analyzer is described in WO99/057561. The analyzer processes samples sequentially. I.e. the samples are transferred from one linear (one dimensional) arrangement of primary sample tubes to another linear arrangement (one dimensional) of test tubes (MTU), and are processed within the analyzer in the sequence in which they were loaded.

The present invention provides for an improved method for isolating analytes, and an improved analytical system.

SUMMARY OF THE INVENTION

The present invention provides for a method for isolating analytes that may be present in fluid samples in an automated analytical system. The method comprises the automated steps of:

a) loading samples on the automated system with identifiers, or identifying loaded samples according to sample type and analytical test to be performed, wherein said sorting is controlled by a control unit;

b) transferring instructions from a control unit to a first and a second pipetting device comprising allocation of individual samples to a two-dimensional n×m arrangement of individual tests in a processing plate;

c) transferring said fluid samples from at least two sample vessels to a at least two vessels of said processing plate with a first pipetting device comprising at least two pipetting units in linear arrangement, wherein said pipetting units are coupled to pipette tips;

d) combining together a solid support material and said fluid sample in a vessel of said processing plate for a period of time and under conditions sufficient to permit said analyte to be immobilized on the solid support material;

e) isolating the solid support material from other material present in the fluid sample in a separation station; and f) purifying the analyte in the separation station by separating the fluid sample from the solid support material and washing the materials one or more times with a wash buffer, wherein said solid support material and said washing buffer are mixed by aspirating and dispensing with a second pipetting device, said second pipetting device comprising pipetting units in an two-dimensional arrangement for coupling to pipette tips;

wherein said pipette tips used in step a) are re-used in step d).

The method of the present invention allows for more efficient processing in the instrument. The sorting of the samples by the control unit enables allocation of individual samples for specific tests within one processing plate. The use of a plate with a two-dimensional arrangement of vessels provides for enhanced throughput since n×m number of samples can be analyzed simultaneously. Thus, in a preferred embodiment of the method of the present invention, said wells of said processing plate are integrally formed. More preferred embodiments are described hereinafter.

BRIEF DESCRIPTION OF THE FIGURES

FIG. 4 shows a perspective view of the Processing Plate.

FIG. 5 shows a perspective view of the Processing Plate from the opposite angle.

FIG. 6 shows a top view of the processing plate.

FIG. 7 shows a cross-sectional view along the longer side of the processing plate.

FIG. 8 shows a partial view of the cross-sectional view.

FIG. 9 shows a perspective view of the longer side of the Processing plate.

FIG. 10 shows a perspective view of the bottom of the Processing plate.

FIG. 11 shows a more vertical perspective view of the bottom of the Processing plate.

FIG. 12 shows the fitting of the smaller magnets of the first preferred embodiment of the separation station with the vessels of the Processing plate.

FIG. 18 a) shows five pipette units connected to one frame part. Four pipette units are in close proximity, the fifth pipette unit is moved independently away from the others. In b) eight pipetting units are shown in close proximity to each other.

FIG. 20 a) to c) show the interface of frame parts with Y-carriage or fixed block.

FIG. 22 a) to c) show examples of sensors.

FIG. 23 shows an analytical system of the present invention

FIG. 24 shows a separation station.

DETAILED DESCRIPTION OF THE INVENTION

Figure 1:
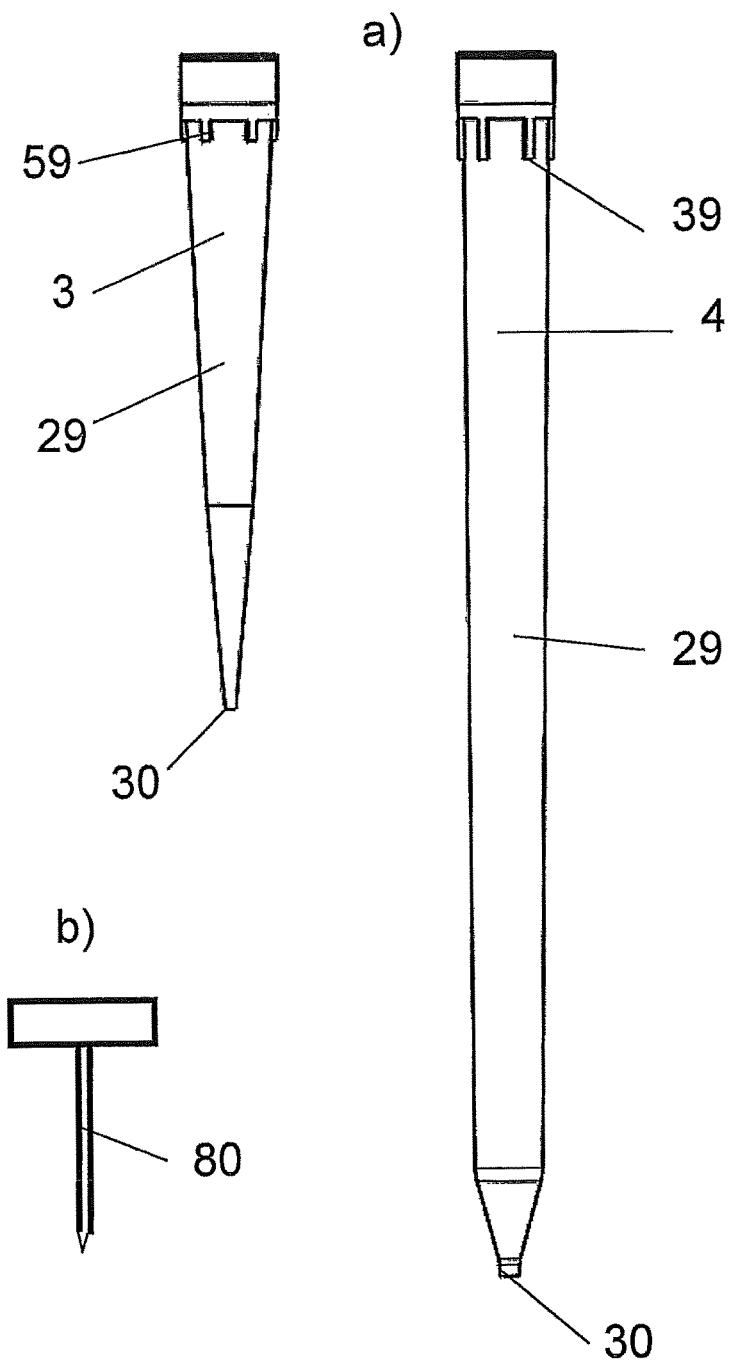
FIG. 1 shows a perspective view of the first and second types of pipette tips. b) Shows a pipette needle.

The present invention provides for a method for isolating analytes that may be present in fluid samples in an automated analytical system. The method comprises the automated steps of:

a) loading samples on the automated system with identifiers, or identifying loaded samples according to sample type and analytical test to be performed, wherein said sorting is controlled by a control unit;

b) transferring instructions from a control unit to a first and a second pipetting device comprising allocation of individual samples to a two-dimensional arrangement of individual tests in a processing plate;

c) transferring said fluid samples from at least two sample vessels to a at least two vessels of a processing plate with a first pipetting device comprising at least two pipetting units in linear arrangement, wherein said pipetting units are coupled to pipette tips;

d) combining together a solid support material and said fluid sample in a well of said processing plate for a period of time and under conditions sufficient to permit said analyte to be immobilized on the solid support material;

e) isolating the solid support material from other material present in the fluid sample in a separation station; and f) purifying the analyte in the separation station by separating the fluid sample from the solid support material and washing the materials one or more times with a wash buffer, wherein said solid support material and said washing buffer are mixed by aspirating and dispensing with a second pipetting device, said second pipetting device comprising pipetting units in a two-dimensional arrangement for coupling to pipette tips;

wherein said pipette tips used in step a) are re-used in step d).

Preferably, step a) additionally comprises sorting of samples loaded on the automated system according to sample type and analytical test to be performed, wherein said sorting is controlled by the control unit in step b). Additionally, step b) may be preceded by entering instructions or transferring information regarding the identity of the samples from a reader to the control device.

The isolating and analyzing samples in two-dimensional n×m arrangement of vessels is advantageous because it allows to isolate and analyse a multitude of samples simultaneously, exposing them to identical conditions, as opposed to sequential processing. Loading samples individually or in a linear array in sequential processing, however, necessitates sorting of samples and transferring of samples from a linear arrangement of sample tubes to a two-dimensional arrangement of processing vessels.

The term "analyte" as used herein may be any type of biomolecule which is of interest for detection, and the detection thereof is indicative of a diagnostic status of an organism. The organism can be animal or, more preferably, human. Preferred analytes are proteins, polypeptides, antibodies or nucleic acids. More preferably, the analyte is a nucleic acid.

The term "isolation" relates to a separation of an analyte from other material present in a liquid sample.

The term "fluid samples" relates to any kind of sample obtainable from an individual which is or can be made available in liquid form for use in the analytical process. Preferred non-limiting examples of such fluid samples are whole blood, plasma, serum, sputum, alveolar lavage, liquefied stool.

The term "sample type" as used herein relates to the type of liquid samples, such as the ones listed above, although the term is understood not to be limited to these types.

The term "analytical test to be performed" relates to the type of analysis to be performed on a specific sample.

Preferred embodiments of a first and a second pipetting device are disclosed hereinafter.

The term "individual samples" as used herein relates to a sample which is or is to be transferred to one specific vessel of the processing plate.

The term "individual tests" relates to a specific test to which a specific individual sample is subjected.

Preferred embodiments of a processing plate are described hereinafter.

The term "vessel" is understood to mean a single vessel or a single vessel in a multi-tube unit, a multiwell plate or a multi-tube unit or a well of a multiwell plate.

Preferred embodiments of a first pipetting device with at least two pipetting units in linear arrangement, wherein said pipetting units are coupled to pipette tips are further described below.

The term "solid support" as used herein relates to any type of solid support to which the analyte is capable of binding, either directly and non-specifically by adsorption, or indirectly and specifically. Indirect binding may be binding of an analyte to an antibody immobilized on the solid support, or binding of a tag to a tag binding compound, e.g. binding of 6×His tags to Ni-chelate. When the analyte is a nucleic acid, such indirect binding is preferably by binding to a capture nucleic acid probe which is homologuous to a target sequence of the nucleic acid of interest. Thus, using capture probes attached on a solid support, a target analyte, preferably a target nucleic acid, can be separated from non-target material, preferably non-target nucleic acid. Such capture probe is immobilized on the solid support. Solid support material may be a polymer, or a composition of polymers. Other types of solid support material include magnetic silica particles, metal particles, etc.

Preferred non-specific binding of nucleic acid to silica particles occurs in the presence of chaotropic compounds. Such binding may also be referred to as direct binding, as opposed to the indirect binding described above. Preferably, the solid supports silica particles which comprise a magnetic or magnetizable material.

"Immobilized on the solid support material" means bound directly or indirectly, as described above.

The analyte bound to the solid support can be separated from other material present. Preferably, the analyte is separated from other material in a separation station by separating the fluid sample from the solid support material and washing the materials one or more times with a wash buffer. An embodiment of a separation station is shown in FIG. 24 and described hereinafter.

Figure 2:
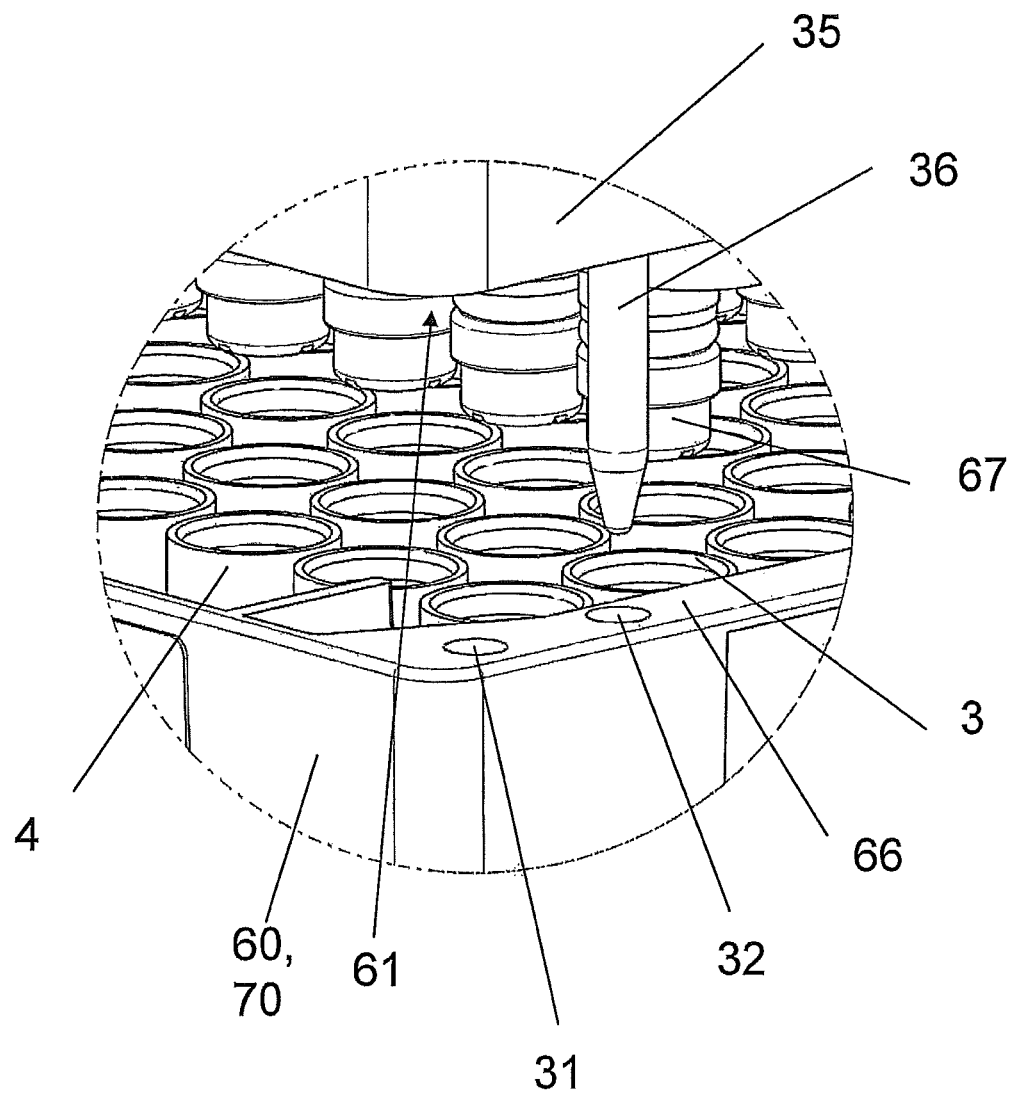
FIG. 2 shows a detailed perspective view of the alignment of the positioning elements on the bottom of the process head and the positioning elements on the top of the upper rack for alignment of the process head with the second type of pipette tips.
Figure 3:
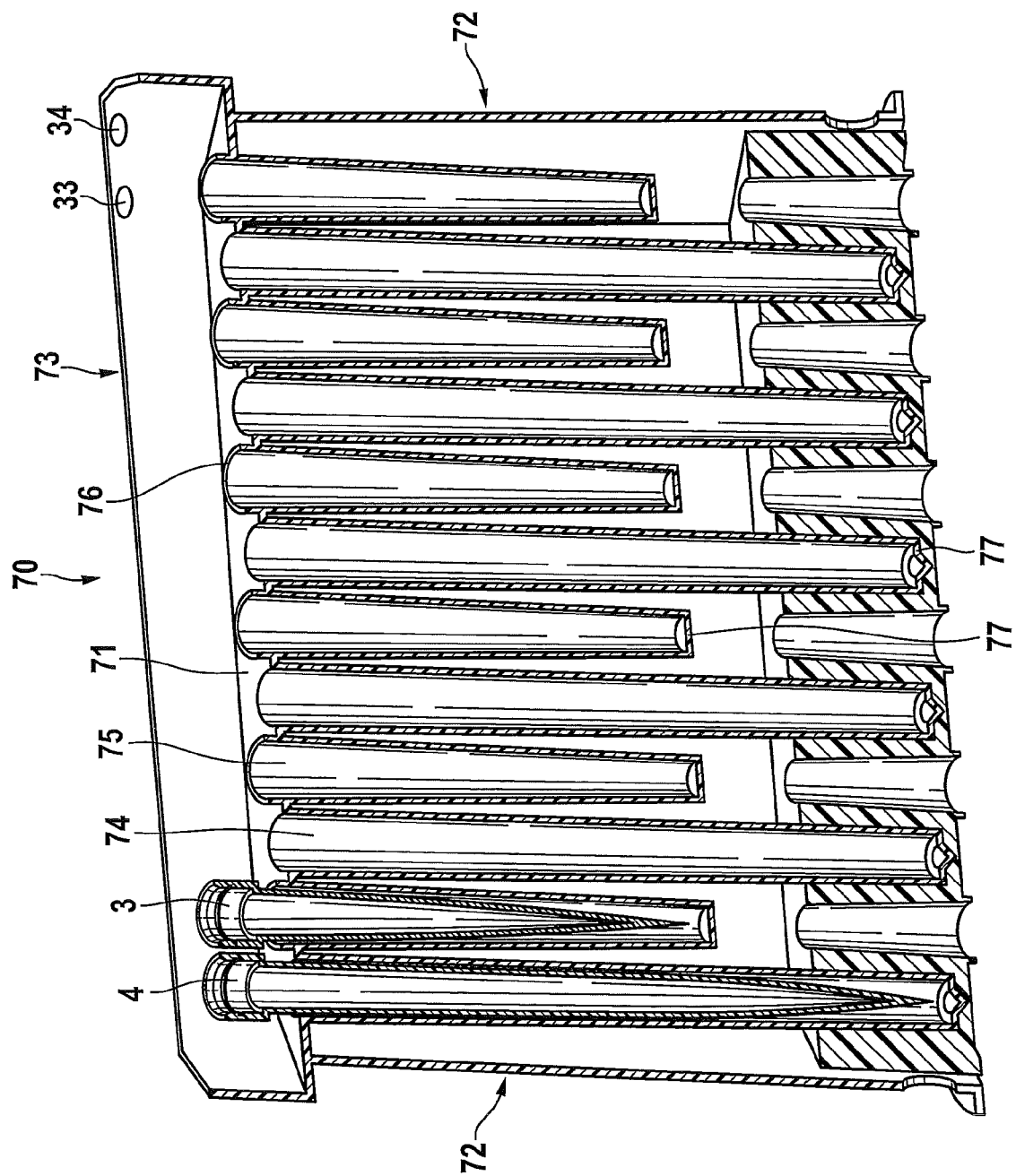
FIG. 3 shows a partial view of a second embodiment of tip rack.
Figure 13:
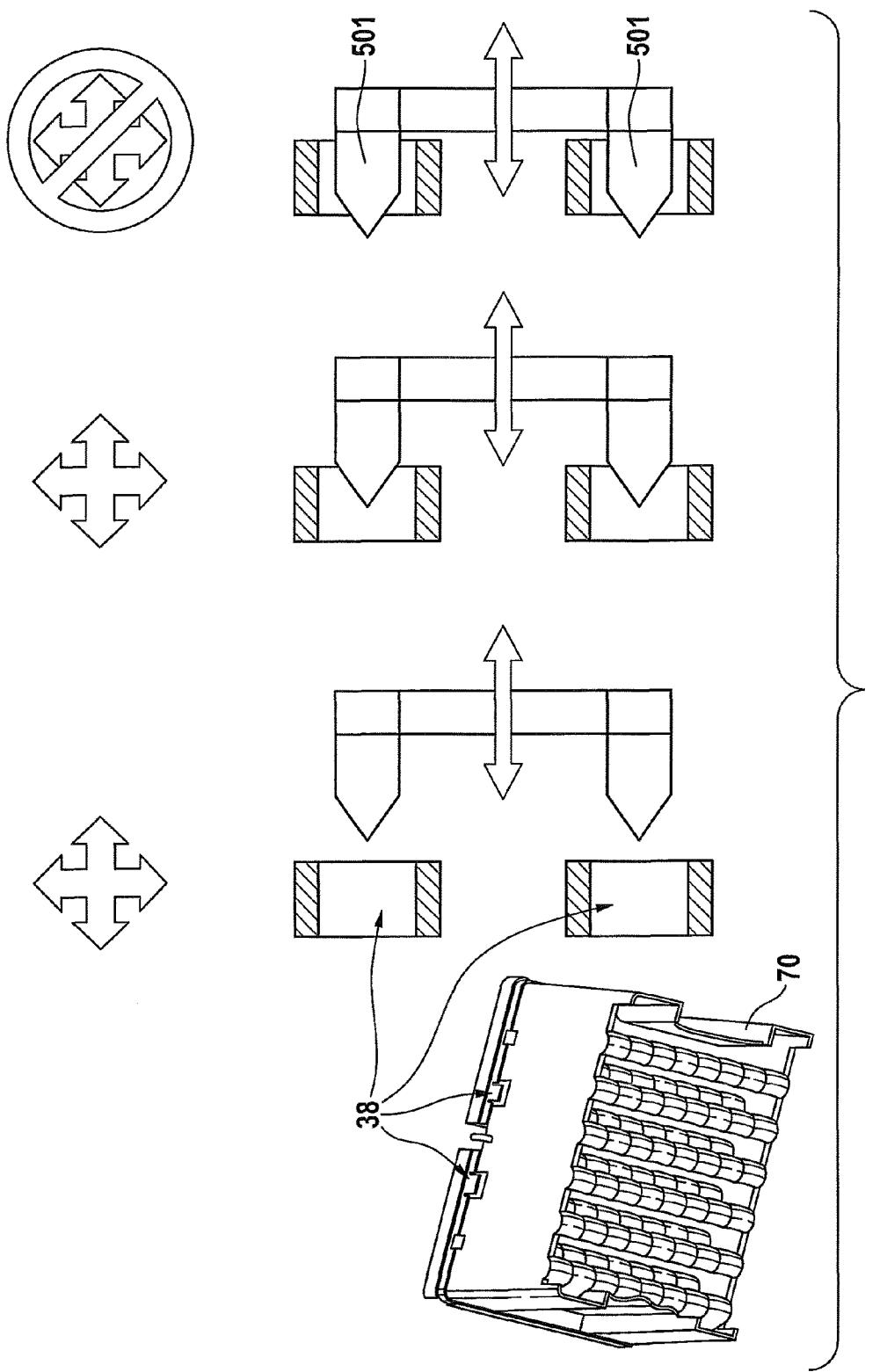
FIG. 13 shows the interaction of a tip rack with the gripper fingers. The form-lock of the gripping prevents movement in X and Y direction (see right hand panel).
Figure 14:
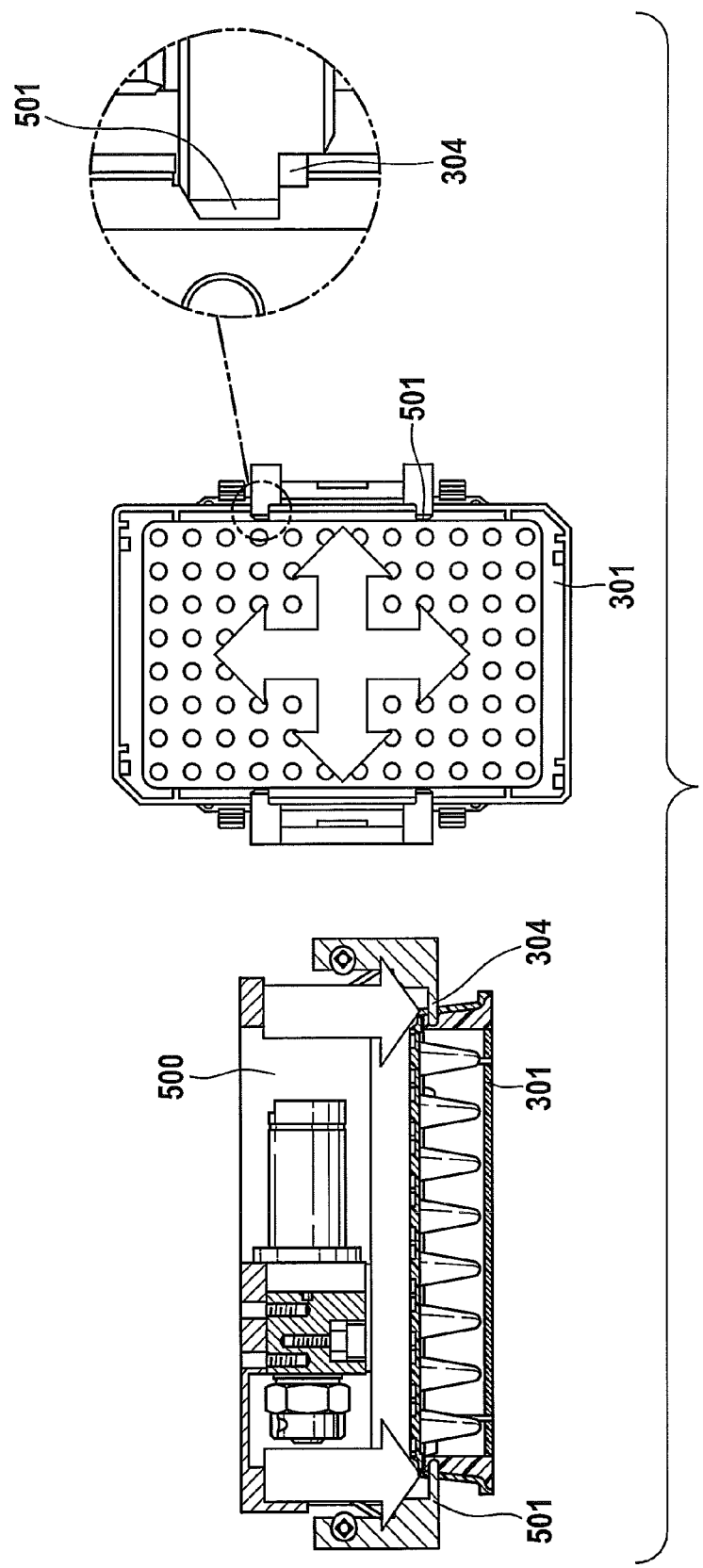
FIG. 14 shows the interaction between the handler and a multiwell plate. The gripper fingers interlock with openings on the multiwell plate, resulting in a form-lock gripping.

A partial view of a preferred embodiment of a second pipetting device is shown in FIG. 2.

More preferably, said processing plate is a multiwell plate with a two-dimensional arrangement of vessels.

Preferably, the sample vessels used in the method of the present invention are arranged in a linear rack.

Sorting of samples is achieved by transfer of information identifying samples to the control unit. Thus, sample vessels comprise stored information relating to their identity and readable by a reader. Preferred embodiments of stored information are barcodes storing information or RFID.

The reader then transfers the information to the control unit. The control unit optimizes the allocation of individual samples for individual tests to be carried out with said samples to the n×m allocation of the vessels in the processing plate. Thus, an optimal use of the processing plates can be achieved by avoiding unnecessary empty vessels in the process plate during the analytical process by optimized sorting and allocation of samples and tests prior to the start of the analytical process. This leads to an optimal throughput according to the requirements of the user and to cost reductions since less consumables are required for a specific number of tests.

In a preferred embodiment of the method herein described, in step b) instructions are transferred from said control unit to a first processor for transferring samples with said first pipetting device, and instructions are transferred from said control unit to a second processor for the steps carried out by said second pipetting device. Furthermore, enhanced efficiency of processing and analysis and cost reductions are achieved because with the specific allocation in the two-dimensional n×m arrangement of samples and tests, the re-use of pipette tips in the first and second position are possible by defining the sample allocation in the two-dimensional n×m arrangement of pipette tips in the pipette tip rack. Preferably, both n and m are >1. Preferably, m>n. In a more preferred embodiment, m>n and n>1 and m>1. More preferably, n is between 2 and 8 and m is between 2 and 12. Most preferably, the present invention comprises a 6×8 arrangement of pipette tips. Preferred embodiments of pipette tip racks are described hereinafter. In a preferred embodiment said pipette tips are replaced in a tip rack in a two dimensional n×m arrangement following step c). The advantageous effect described hereinbefore is achieved by the step of assigning any one pipette tip in said pipette tip rack to a specific vessel of said processing plate with a two-dimensional n×m arrangement of vessels. Preferably, a pipette tip located in position ny/mz of the two-dimensional n×m arrangement of the pipette tip rack is used for pipetting a sample to the vessel in position ny/mz of the two-dimensional n×m arrangement of vessels in said processing vessel.

In a preferred embodiment, the plate has a two dimensional n×m arrangement of the vessels, and the pipette rack has a two-dimensional a×n×m arrangement of vessels, wherein a is equal or larger than 1. Embodiments of a>1 are disclosed herein. Preferably, in such embodiments, pipette tips of two types, i.e., pipette tips of a larger volume and pipette tips of a smaller volume as disclosed herein are included in the tip rack.

Preferred embodiments of second pipetting devices comprise process heads with a two-dimensional n×m arrangement of pipetting units. Preferably, both n and m are >1. Preferably, m>n. In a more preferred embodiment, m>n and n>1 and m>1. More preferably, n is between 2 and 8 and m is between 2 and 12. Most preferably, the present invention comprises a 6×8 arrangement of pipetting units. Pipetting units are understood to comprise interfaces for interacting with a pipette tip. They further comprise an actuator, preferably a pump for aspirating and dispensing liquids.

In a preferred embodiment, the distance between two adjacent sample vessels is different from the distance between two adjacent vessels of the processing plate, and wherein the distance between two adjacent pipetting units of the first pipetting device is adjustable. Preferred embodiments of said first pipetting device are described hereinafter.

It is important to understand that the two-dimensional arrangement of pipette tips is a two dimensional matrix arrangement which is not linear (i.e. n and m are >1).

Preferably, the method additionally comprises the step of analyzing said purified analyte.

The present invention also relates to an analytical system (440) for processing an analyte, comprising:

a) a first position comprising first receptacles (1001) in linear arrangement comprising liquid samples (1010), a processing plate (101) comprising receptacles (103) in two-dimensional arrangement for holding a liquid sample (1011), a first pipetting device (700) comprising at least two pipetting units (702) in linear arrangement, wherein said pipetting units (702) are coupled to pipette tips (3, 4), and a tip rack (70) comprising pipette tips (3, 4) in a two-dimensional a×(n×m) arrangement;

b) a second position comprising a holder (201, 128) for said processing plate (101), a holder (470) for said tip rack (70) and a second pipetting device (35), said second pipetting device (35) comprising pipetting units (702) in a two-dimensional arrangement for coupling to pipette tips (3, 4) (FIG. 23). The term "holder" as used herein relates to any arrangement capable of receiving a rack or a processing plate. In one embodiment, said holder is a processing station (201). In another embodiment, said holder is a heating device (128). A schematic embodiment of a system according to the present invention is shown in FIG. 23. In one embodiment, the first position is a module for preparing samples for processing (402), and the second position is a processing module (401) which is understood to be a module for isolation and purification of an analyte.

First receptacles (1001) are preferably placed in a rack (1002). The first position preferably comprises a holder (1003) for rack (1002).

The first position additionally preferably comprises a holder (1007) for rack (70).

The advantages of the analytical system (440) of the present invention are as described above for the method of the present invention.

Preferably, the position of said pipetting units (702) of the first pipetting device (700) are variable. Preferred embodiments of said first pipetting device (700) are described hereinafter.

In one embodiment, the tip rack (70) comprises pipette tips (3, 4) in a two-dimensional a×(n×m) arrangement. Preferably, a first type (4) and a second type (3) of pipette tips are comprised in the tip rack (70). In this embodiment, the first type of pipette tips (4) is arranged in a two-dimensional arrangement, and the second type of pipette tips (3) is arranged in the two-dimensional arrangement. More preferably, the first type of pipette tips (4) has a different volume than the second type of pipette tips (3), preferably, the volume of the first type of pipette tips (4) is more than 500 ul, and the volume of the second type of pipette tips (3) is less than 500 ul. In this embodiment, a=2. More preferably, the volume of the first type of pipette tips is between 0.5 ml and 5 ml, and the colume of the second type of pipette tips is between 0.5 ul to 500 ul. However, embodiments of the invention with more than two types of pipette tips, and thus a >2 are also included in the present invention.

In one aspect, the analytical system (440) of the present invention comprises a control unit (1006) for allocating sample types and individual tests to individual positions of said processing plate (101). Preferably, said positions are separate cells (401, 402).

In one aspect of the invention, the system additionally comprises a transfer system (480) for transferring said process plate (101) and said rack (70) between first (402) and second (401) positions. Preferred embodiments of said transfer system (480) are conveyor belts or, more preferably, one or more handler. Preferred embodiments of said handler are described hereinafter.

Furthermore, preferably said pipette units of said second pipetting device (35) are engaged to pipette tips (3, 4) which were used in the first position (402).

A preferred embodiment of the system (440) of the present invention additionally comprises a third station (403) comprising a temperature-controlled incubator for incubating said analyte with reagents necessary to obtain a detectable signal. Further preferred embodiments of this system are described hereinafter.

More optimal control of the allocation of samples and tests to the two-dimensional arrangement is achieved with a first processor (1004) which is comprised in said first position (402) to which said control unit (1006) transfers instructions for allocating sample types and individual tests to specific positions in the two-dimensional arrangement of vessels (103) of the process plate (101), and a second processor (1005) which is comprised in said second position (401) to which said control unit (1006) transfers instructions for allocating sample types and individual tests to specific positions in the two-dimensional arrangement of vessels (103) of the process plate.

Preferably, said system additionally comprises a first processor located in said first position, and a second processor located in said second position.

More preferably, said first processor (1004) controls said first pipetting device (700) and said second processor (1005) controls said second pipetting device (35).

Re-Use of Pipette Tips

In one aspect, the invention relates to a method for isolating and analyzing an analyte that may be present in a fluid sample. Said method comprises the automated steps of:

a) transferring said fluid sample from a sample vessel to a processing vessel with a pipette tip;

b) combining together a solid support material and said fluid sample in a well of said processing vessel for a period of time and under conditions sufficient to permit said analyte to be immobilized on the solid support material;

c) isolating the solid support material from other material present in the fluid sample in a separation station;

d) and purifying the analyte in the separation station by separating the fluid sample from the solid support material and washing the materials one or more times with a wash buffer.

Preferably, said pipette tip used in step a) is re-used after step a).

In a preferred embodiment of the method hereinbefore described, step a) comprises:

a1) engaging pipette tips of a first type which are held in a rack in a first position with a first process head;

a2) transferring said fluid sample from a sample vessel to a processing vessel with pipette tips of a first type engaged to a first process head;

a3) placing said pipette tips in said rack and disengaging said pipette tips from said process head;

a4) transporting said rack comprising said pipette tips and said processing vessel to second positions;

a5) engaging said pipette tips of a first type which are held in said rack with a second process head in said second position.

Preferably, the processing vessel comprises more than one receptacle. More preferably, the processing vessel is a multiwell plate. The method preferably additionally comprises the step of:

e) reacting said purified analyte with reagents necessary to obtain a detectable signal.

Re-use of pipette tips leads to a reduction of disposable consumables used in the analytical method and to cost reductions. In a preferred embodiment, the washing in step d) comprises aspirating and dispensing the washing buffer with a process head engaged to pipette tips.

The term "receptacle" as used herein relates to a single vessel (or tube) or to a tube comprised in a multi-tube unit, or to a well (or vessel) of a multiwell plate.

In a preferred embodiment, the reacting comprises generating a detectable signal. More preferably, the method additionally comprises the step of detecting a detectable signal.

The term "reacting" as used herein relates to any type of chemical reaction of the analyte with reagents that is necessary to obtain a detectable signal. Preferably, said reacting comprises amplification. Amplification may be understood as any type of enhancement of a signal. Thus, amplification can be a conversion of a molecule by an enzyme, wherein said enzyme is coupled or bound to the analyte, leading to a detectable signal, wherein more signal molecules are formed than analyte molecules are present. One such non-limiting example is a formation of a chemiluminescent dye, e.g. using ECL. The term amplification further relates to nucleic acid amplification, if the analyte is a nucleic acid. This includes both linear, isothermal and exponential amplifications. Non-limiting examples of nucleic acid amplification methods are TMA, SDA, NASBA, PCR, including real-time PCR. Such methods are well known to the skilled person.

In a preferred embodiment of the method hereinbefore described, the transporting of said rack comprising said pipette tips and said processing vessel to a second positions occurs between a separate first cell of an analytical instrument and a separate second cell, preferably a processing cell, of said analytical system. Preferably, the rack comprises independent chambers to accommodate pipette tips.

In a preferred embodiment, the first type of pipette tips is re-used for the washing in step d).

In a preferred embodiment, the rack additionally comprises a second type of pipette tips. Further preferred is a method as hereinbefore described, wherein between step d) and e), the analyte is eluted from the magnetic particles. A preferred embodiment comprises the transfer of the analyte from said processing vessel, which is preferably a multiwall plate, to a reaction vessel, which is preferably a multiwall plate, with said second type of pipette tips.

Preferred Automated Analytical System

In a preferred aspect, the system of the present invention comprises:

a) a first position comprising a first receptacle holding a liquid sample comprising an analyte, a second receptacle for holding a liquid sample, a rack holding pipette tips, and a first process head for transferring a liquid sample from the first receptacle to a second receptacle, b) a second position comprising a station for receiving said second receptacle, and a rack holding station for receiving said rack, c) a transfer system for transferring the second receptacle and the rack holding pipette tips between the first position and the second position.

Preferably, the positions are separate cells. The rack transferred by said transfer system preferably comprises pipette tips which were used in the first position. In a preferred embodiment, the first receptacle is a sample vessel and the second receptacle is a processing vessel. Further preferred is a processing vessel which is a multiwell vessel. Preferred embodiments of said stations are described hereinafter.

In the analytical system herein described, the transport system preferably transfers the receptacle and the rack from the first position to the second separate position. Preferably, the second separate position comprises a magnetic separation station. The analytical system additionally preferably comprises an amplification station.

The transport system of the preferred system comprises a handler constructed and arranged to grip and transport said rack and said processing vessel from a first to a second location within the system. Further preferred handlers are disclosed herein.

The system is preferably fully automated.

The automated analyzer further comprises a reaction station disposed in a third location, wherein said reaction station is constructed and arranged to analyze said analyte to obtain a detectable signal. Another preferred embodiment of a reaction station is a station comprising an incubator. Preferably, said incubator is a temperature-controlled incubator. More preferably, said incubator is held at one constant temperature. Another preferred embodiment of an incubator is a thermocycler block. Preferably, a detector for detecting the detectable signal is integrally connected to the reaction station, more preferably to the incubator as hereinbefore described. A preferred detector comprises a nucleic acid quantification system for periodic measurement and quantification. More preferably, the detector additionally comprises a nucleic acid detection system which detects the signal and ascertains the presence or absence of the nucleic acid in the reaction receptacle based upon whether or not a signal above a threshold level is detected.

Alternatively, the automated analyzer additionally comprises a detecting station. The automated analyzer further comprises a transport mechanism. Said transport mechanism comprises a handler for handling consumables. Said handler preferably transports a consumable between stations. In one embodiment, said transport mechanism is constructed and arranged to transport said sample vessel and said rack from said sample dispensing station to said separation station. Further preferred embodiments of the automated analyzer of the present invention are individual or combined features disclosed herein.

In a preferred embodiment, the analytical apparatus (400) of the present invention comprises at least one module (401) for processing an analyte, said processing comprising pipetting of a liquid. The processing module (401) comprises:
 a) a process head (35) for engaging with pipette tips (3, 4), said process head (35) comprising positioning elements (36) arranged in the lower surface (61) of said process head (35),
 b) a tip rack (60, 70) holding pipette tips (3, 4), wherein said tip rack (60, 70) comprises positioning elements (31, 32, 33, 34) capable of engaging mechanically with the positioning elements (36) on the process head (35).

In a preferred embodiment of the analytical apparatus (400) hereinbefore described, said processing module (401) is a module for isolation and purification of an analyte. Therefore, the term "processing" as used herein is understood to relate to isolation and/or separation and/or capture and/or purification of an analyte. Preferably, said apparatus (400) comprises a module for preparing samples for processing (402). Preferably, said apparatus (400) comprises a module for amplification of said analyte (403). In one preferred embodiment, said apparatus additionally comprises a module (404) for transferring amplification reagents from a storage receptacle to a receptacle comprising a purified analyte. Further preferred embodiments of said apparatus are as hereinbefore and hereinafter described.

The present invention also relates to an automated analyzer (400) for use in performing a nucleic acid based amplification reaction, said analyzer comprising a plurality of modules (401, 402, 403). One module is a processing module disposed at a first location within the analyzer constructed and arranged to separate a nucleic acid from other material in a sample. Said processing module comprises a separation device as herein described. The analyzer further comprises an amplification module disposed and arranged at a second location within the analyzer. The amplification module comprises a temperature-controlled incubator for incubating the contents of at least one receptacle, preferably of a multiwell plate comprising the separated nucleic acid and one or more amplification reagents for producing an amplification product indicative of the target nucleic acid in the sample.

The term "module" and "cell" are used interchangeably herein.

Preferred Embodiment of a Tip Rack

A preferred embodiment of an exemplary tip rack is an integral one part tip rack (70) comprising a top surface (71), two opposing short (72) and two opposing long (73) side walls (FIG. 2). The tip rack comprises vessels (74, 75) for holding pipette tips (3, 4). Said vessels (74, 75) comprise an open top (76) and a closed bottom (77). Any one vessel (74, 75) can hold one tip (3, 4). The footprint of the rack (70) preferably comprises a length and width of the base essentially corresponding to ANSI SBS footprint format. More preferably, the length is 127.76 mm+/−0.25 mm, and the width is 85.48 mm+/−0.25 mm. Preferred embodiments of said second embodiment comprise hardware identifiers (6, 7, 39), recesses (37) to engage with counter elements on an analytical instrument to hold down the rack in the instrument as described for the first embodiment of said rack. Preferred embodiments also comprise positioning elements (31, 32, 33, 34, 10) as described for the first embodiment of the rack (60).

Multiwell Plate/Processing Plate

The processing plate (101) of the present invention is preferably a 1-component plate. Its top surface (110) comprises multiple vessels (103) (FIG. 4-6). Each vessel has an opening (108) at the top and is closed at the bottom end (112). The top surface (110) comprises ribs (104) which are preferably elevated relative to the top surface (110) and surround the openings (108) of the vessels (103). This prevents contamination of the contents of the vessels (103) with droplets of liquid that may fall onto the top surface (110) of the plate (101). Views of a preferred process plate are shown in FIGS. 4 to 13.

The footprint of the processing plate (101) preferably comprises a length and width of the base corresponding to ANSI SBS footprint format. More preferably, the length is 127.76 mm+/−0.25 mm, and the width is 85.48 mm+/−0.25 mm. Thus, the plate (101) has two opposing shorter side walls (109) and two opposing longer side walls (118). The processing plate (101) comprises form locking elements (106) for interacting with a handler (500). The processing plate (101) can be gripped, transported and positioned quickly and safely at high speed while maintaining the correct orientation and position. Preferably, the form locking elements (106) for gripping are located within the upper central part, preferably the upper central third of the processing plate (101). This has the advantage that a potential distortion of the processing plate (101) has only a minor effect on the form locking elements (106) and that the handling of the plate (101) is more robust.

The processing plate (101) preferably comprises hardware-identifiers (102) and (115). The hardware identifiers (102) and (115) are unique for the processing plate (101) and different from hardware identifiers of other consumables used in the same system. The hardware identifiers (102, 115) preferably comprise ridges (119) and/or recesses (125) on the side walls of the consumables, wherein said pattern of ridges (119) and/or recesses (125) is unique for a specific type of consumable, preferably the processing plate (101). This unique pattern is also referred to herein as a unique "surface geometry". The hardware-identifiers (102, 115) ensure that the user can only load the processing plate (101) into the appropriate stacker position of an analytical instrument (126) in the proper orientation. On the sides of processing plate (101), guiding elements (116) and (117) are comprised (FIG. 11). They prevent canting of the processing plate (101). The guiding elements (116, 117) allow the user to load the processing plates (101) with guiding elements (116, 117) as a stack into an analytical instrument which is then transferred vertically within the instrument in a stacker without canting of the plates.

Between the rows (123) of vessels (103), a continuous space (121) is located (FIG. 10, 11). The space (121) can accommodate magnets (122) or heating devices (128).

At the upper end of the vessels (103), one of the shorter side walls (109) of the vessel (103) comprises an reagent inlet channel (105) which extends to the circumferential rib (104) (FIG. 4). The reagents are pipetted onto the reagent inlet channel (105) and drain off the channel (105) into the vessel (103). Thus, contact between the pipette needle (80) or tip (3, 4) and liquid contained in the vessel is prevented. Furthermore, splashes resulting from liquid being directly dispensed into another liquid (215) contained in the vessels (103), which may cause contamination of the pipette needle (80) or tip (3, 4) or neighboring vessels (103) is prevented. Sequential pipetting onto the reagent inlet channel (105) of small volumes of reagents followed by the largest volume of another reagent ensures that the reagents which are only added in small amounts are drained completely into the vessel (103). Thus, pipetting of small volumes of reagents is possible without loss of accuracy of the test to be performed.

On the inside, on the bottom of the vessels (111, 112), the shape becomes conical (111) and ends with a spherical bottom (112) (FIG. 10). The inside shape of the vessel (114), including the rectangular center part (120), is rounded. The combination of spherical bottom (112), rounded inside shape (114), conical part (111) and refined surface of the vessels (103) leads to favorable fluidics which facilitate an effective separation and purification of analytes in the processing plate (101). The spherical bottom (112) allows an essentially complete use of the separated eluate and a reduction of dead-volume which reduces the carryover of reagents or sample cross-contamination.

The rim on the base (129) of the processing plate (101) comprises recesses (107) for engagement with latch clips (124) on the processing station (201) or heating device (128) or analytical instrument (126). The engagement of the latch clips (124) with the recesses (107) allows positioning and fixation of the processing plate (101) on the processing station (201). The presence of the recesses (107) allows the latch force to act on the processing plate (101) almost vertically to the base (129). Thus, only small forces acting sideways can occur. This reduces the occurrence of strain, and, thus, the deformation of the processing plate (101). The vertical latch forces can also neutralize any deformations of the processing plate (101) leading to a more precise positioning of the spherical bottoms (111) within the processing station (201). In general, the precise interface between the processing plate (101) and the processing station (201) or heating device (128) within an analyzer (126) reduces dead-volumes and also reduces the risk of sample cross-contamination.

Handler

A preferred handler (500) comprises a central part (500*a*) which is connected to a robotic arm (502). The central part (500*a*) comprises, on two opposite sides, gripper fingers (501). The gripper fingers (501) are movable. When engaging with a consumable (60, 70, 101, 301, 302) comprising form-locking elements (38, 106, 507, 309), as hereinbefore described, the gripper fingers (501) connect with the consumable (60, 70, 101, 301, 302). The gripper fingers (501) are moved towards the consumable (60, 70, 101, 301, 302), in X-direction, interlock with the form locking elements (38, 106, 507, 309), until the gripper fingers (501) reach a stop. In this position, a form-locked position between handler (500) and consumable (60, 70, 101, 301, 302) exists. The handler (500) connected to the robotic arm (502) can move the consumable (60, 70, 101, 301, 302) from one position to a second position. To release the consumable (60, 70, 101, 301, 302), the gripper fingers (501) move away from the consumable (60, 70, 101, 301, 302). Preferably, the handler comprises spring-mounted pins (506). Said pins (506) are forced away from the consumable (60, 70, 101, 301, 302) when the handler (500) is pushed on the consumable (60, 70, 101, 301, 302). In this position, the gripper fingers (501) can interact with the form locking elements (38, 106, 507, 309) of the consumable (60, 70, 101, 301, 302). When pressing the handler (500) down on the consumable (60, 70, 101, 301, 302), the gripper fingers (501) can move away from the form locking elements (38, 106, 507, 309) of the consumable (60, 70, 101, 301, 302) (FIG. 15 *a*)).

Figure 15:
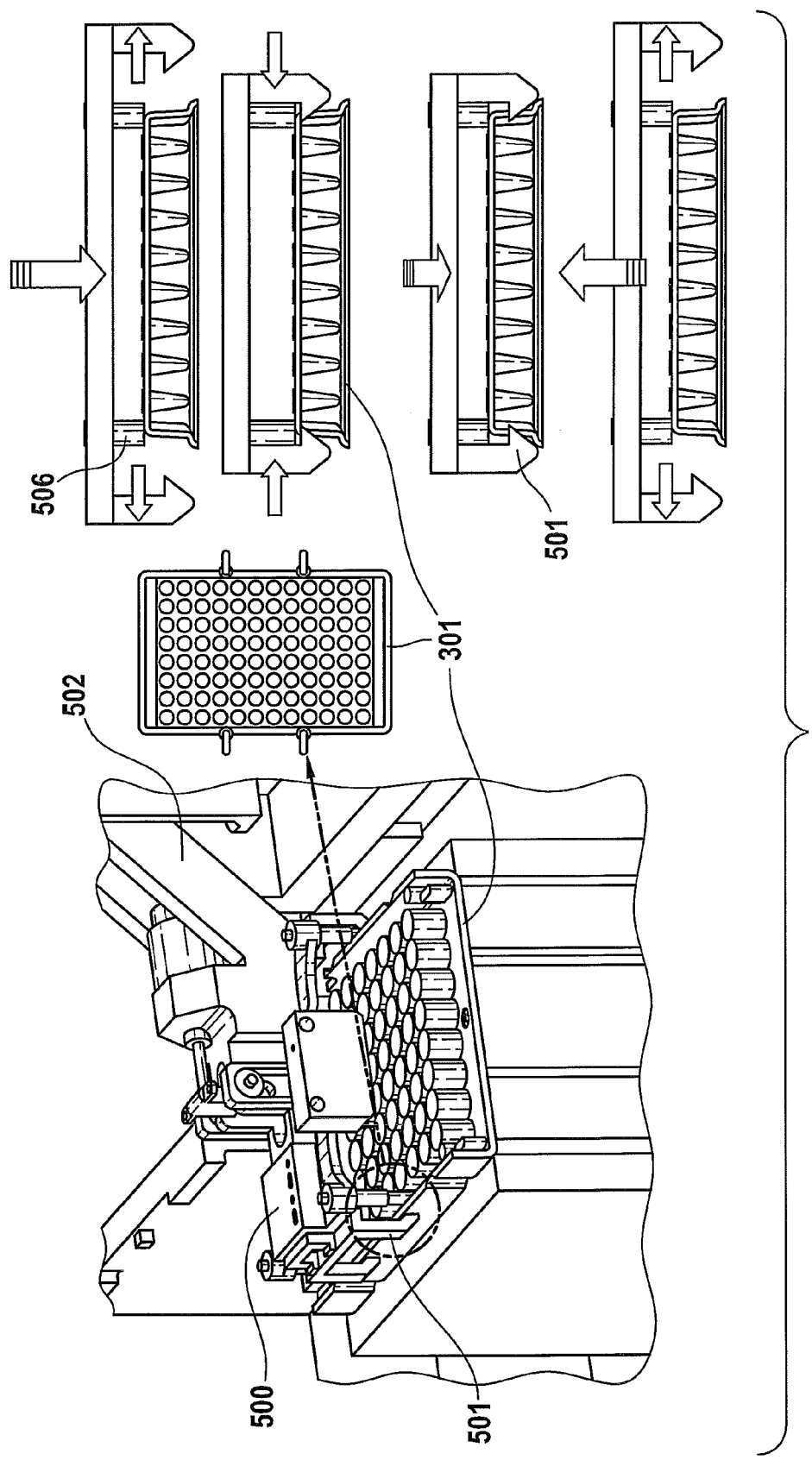
FIGS. 15 a) and b) show the handler connected to a robotic arm, and the attachment and release of the consumable by the gripper fingers. c) Shows that the handler interacts with different consumable with the same interface.
Figure 15:
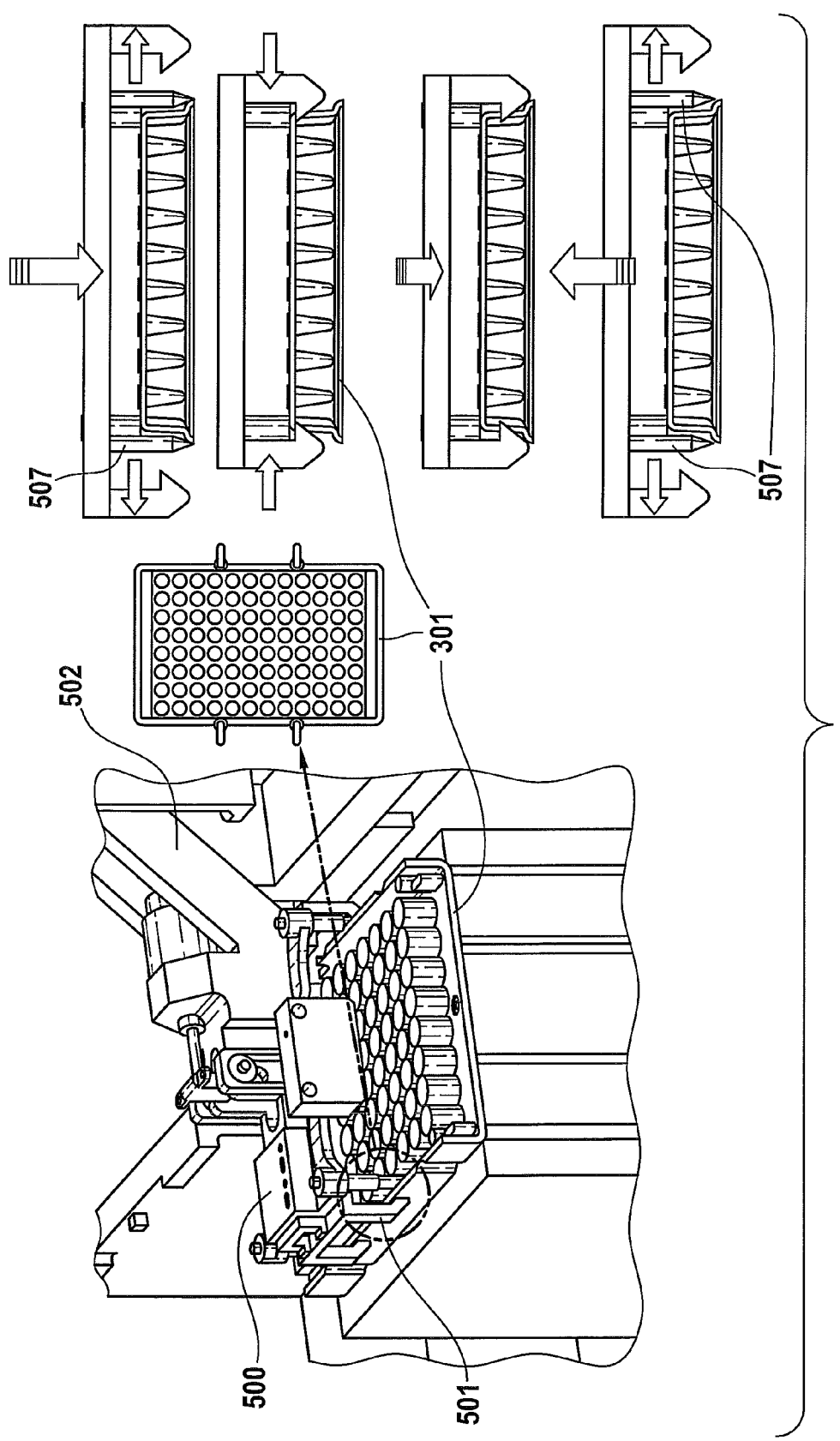
Figure 15:
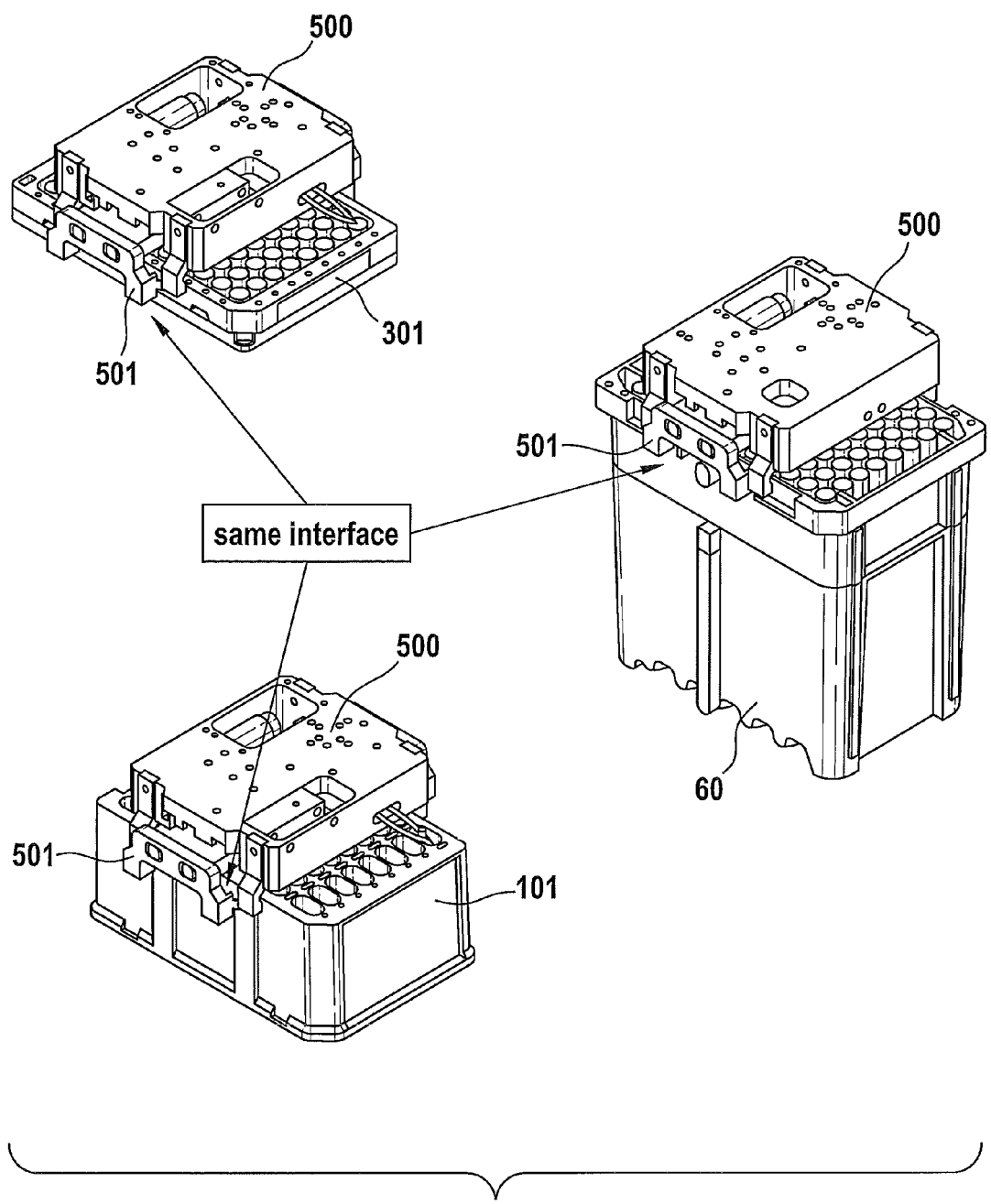

The handler (500) also comprises pins (507) which are located sideways of the multiwell plate when the handler (500) is moved downwards on the consumable (60, 70, 101, 301, 302) prior to gripping. These pins (507) guide the consumable (60, 70, 101, 301, 302) into the correct position for gripping. Furthermore, said pins (507) prevent the consumable (60, 70, 101, 301, 302) from getting stuck to the handler (500) when the gripper fingers (501) move away from the consumable (60, 70, 101, 301, 302) (FIG. 15 *b*)

Preferably said form-locking elements (38, 106, 507, 309) are openings (38, 106, 507, 309) in the side walls of the consumable, more preferably the long side of the consumable (60, 70, 101, 301, 302). Preferably, two openings (38, 106, 507, 309) are located on one side wall, and two openings (38, 106, 507, 309) are located on the opposite side wall.

Preferred Embodiment of a First Pipetting Device

In one embodiment, at least one module is mounted outside of said frame, wherein the said modules of two adjacent pipetting units are staggered. This again allows achieving an appropriate spacing between said pipetting units. In another embodiment, the pipetting unit does not comprise frames. In this embodiment, at least one module is mounted in a staggered fashion on two adjacent pipetting units.

A preferred shortest distance between said more than one pipette units is 10 mm or shorter. More preferably, the shortest distance between said more than one pipette units is between 10 mm and 1 mm. Further preferred shortest distances are 9 mm, 4.5 mm, 2.25 mm, 1.125 mm.

In a preferred embodiment, the device hereinbefore described additionally comprises a sixth module, which is a sensor module. Preferred sensor modules are sensors for initializing or determining the position in Y or Z direction of the pipette unit. Preferred sensors for determining the position of the pipette unit in is a ultrasound sensor.

Preferably, one side of a pipette unit is connected to said Y-axis transfer mechanism.

Preferably, said pipette units additionally comprise ball bearings, wherein said ball bearings of two adjacent pipette units are staggered.

The present invention further relates to a method of pipetting samples from a first set of vessels holding said samples to a second set of vessels, wherein the distance between adjacent vessels of the first set of vessels is different from the distance between adjacent vessels of the second set of vessels. Said method comprises aspirating said samples with pipette tips mounted on a device hereinbefore described, wherein the distance between said pipetting units is adjusted to the distance between said first set of vessels by moving the pipetting units along one axis prior to aspiration. The distance between the pipette units to the distance between said second set of vessels prior to dispensing is then adjusted for dispensing said samples into the second set of vessels.

In a preferred embodiment of the method hereinbefore described, said first set of vessels comprises at least two vessels in a linear arrangement. Preferably, said second set of vessels are integrally formed. In another preferred embodiment, the second set of vessels is only one vessel. In a more preferred embodiment, said second set of vessels comprises a multiwell plate.

The present invention further relates to a method of isolating and analyzing at least one analyte that may be present in at least one liquid sample in an automated analytical system, comprising the automated steps of providing a first set of vessels comprising said at least one liquid sample to said automated analytical system; aspirating at least a portion of said at least two liquid samples from said first set of vessels with a pipetting device comprising more than one pipetting unit, wherein the distance between said pipetting units is adjusted to the distance between the first set of vessels prior to aspiration; adjusting the distance between said pipetting units to the distance between vessels of a second set of vessels; dispensing said liquid samples into said second set of vessels. The method further comprises the steps of combining together a solid support material and one of said fluid samples in a well of said second set of vessels vessel for a period of time and under conditions sufficient to permit said analyte to be immobilized on the solid support material. isolating the solid support material is then isolated from other material present in the fluid sample in a separation station. The analyte is then purified in the separation station by separating the fluid sample from the solid support material and washing the materials one or more times with a wash buffer. Finally, the analyte is analyzed. In a preferred embodiment, the method comprises at least two liquid samples. In another preferred embodiment, said analyte is a nucleic acid. More preferably, said device comprises the device hereinbefore described.

The present invention also relates to an analytical system for isolating an analyte, comprising a module for transferring samples from a first set of vessels to a second set of vessels, wherein said module comprises a pipetting device comprising more than one pipetting units, wherein said pipetting units are movable relative to each other along one axis; and a module for isolating said analyte. Preferably, said analytical system additionally comprises a module for analyzing said analyte.

Figure 16:
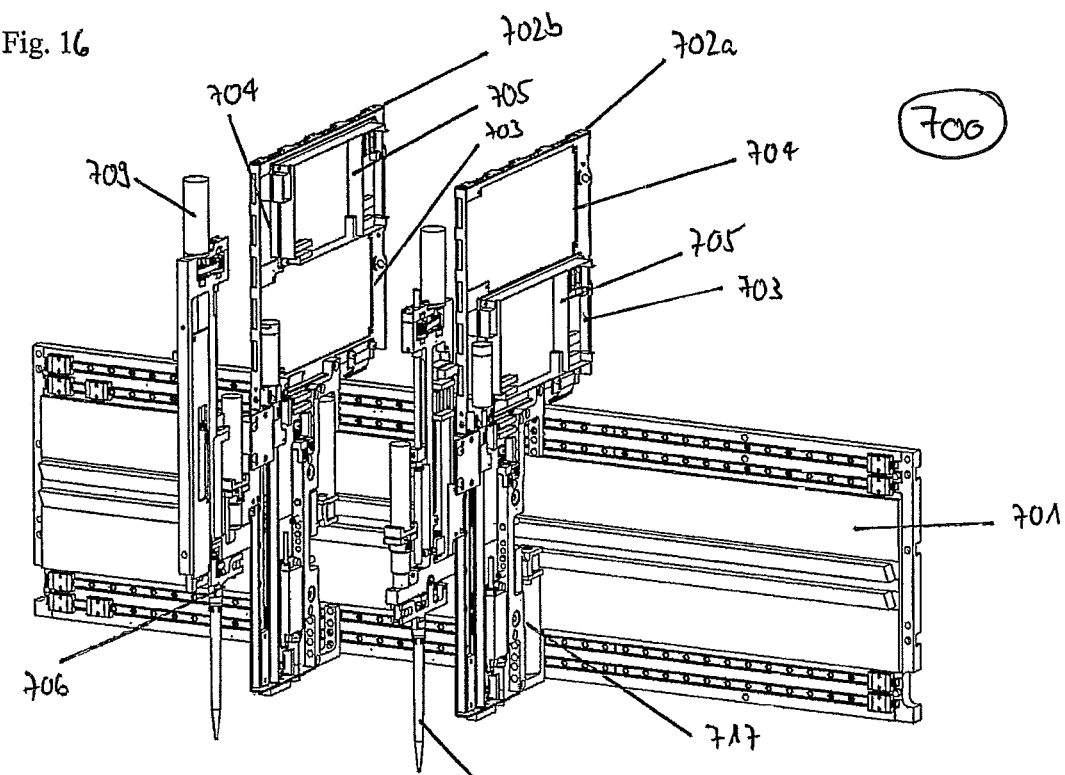
FIG. 16 shows two pipette units with staggered modules connected to a frame part.

A device (700) according to the invention comprising a main frame body (701) and two pipetting units (702 a, b) is shown in FIG. 16. Each pipetting unit (702) comprises two frames (703, 704). In the non-limiting example shown in FIG. 16, any one of the pipetting unit (702) comprises an electronic module (705). The electronic module (705) of pipetting unit (702 a) is mounted in the lower frame (703), the electronic module (705) of pipetting unit (702 b) is mounted in the upper frame (704). The Y-axis actuators (717) are also mounted on the pipetting units in a staggered fashion. The pipetting units also comprise interfaces (706) for interacting with pipette tips (3, 4).

Figure 17:
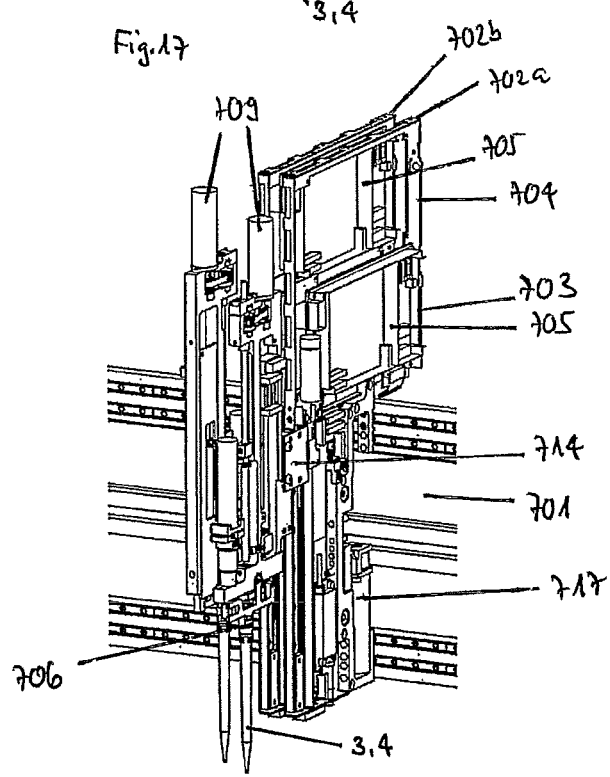
FIG. 17 shows two pipette units moved into close proximity of each other.

FIG. 17 shows the two units (702 a, b) as they are moved together, bringing the two pipette tips (3, 4) into close proximity. Corresponding modules (e.g., 705) are arranged in an non-overlapping way to allow for an optimal spacing between the two pipetting units. FIG. 18 a) shows a device (700) with five pipette units (702 a to e) with the staggered mount of different modules (705). Four of the pipette units (702 b to e) are shown with a short distance between each other. The fifth unit (702 a) is shown in a position further away. FIG. 18 b) shows a device (700) with eight pipetting units (702), wherein all units (702) are in close proximity to the adjacent units (702) and have needles (80) for pipetting.

Figure 19A:
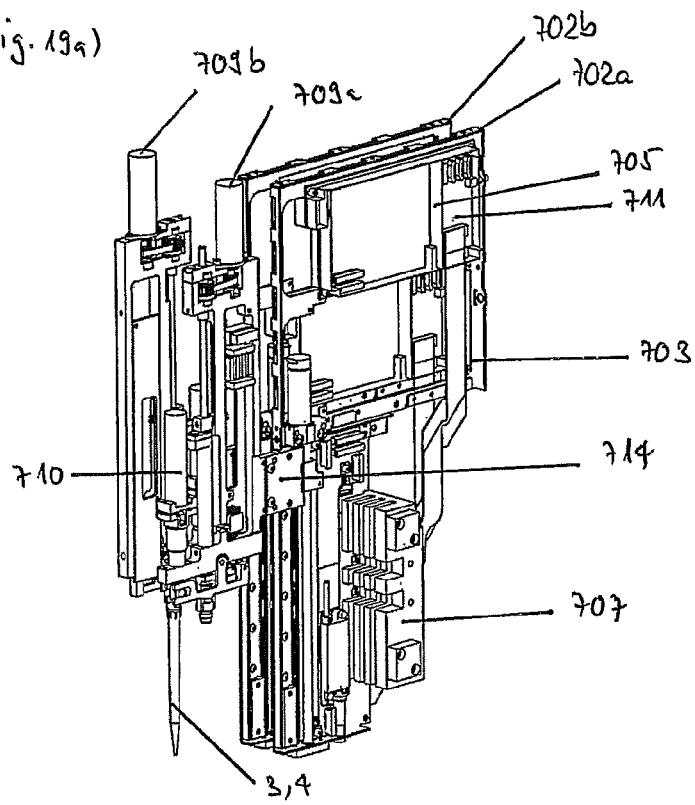
FIG. 19 shows a device with two units fixed to a support for movement in Z-direction, but not in Y-direction (a). In b) shows the two units from a) with individual parts separated.
Figure 19B:
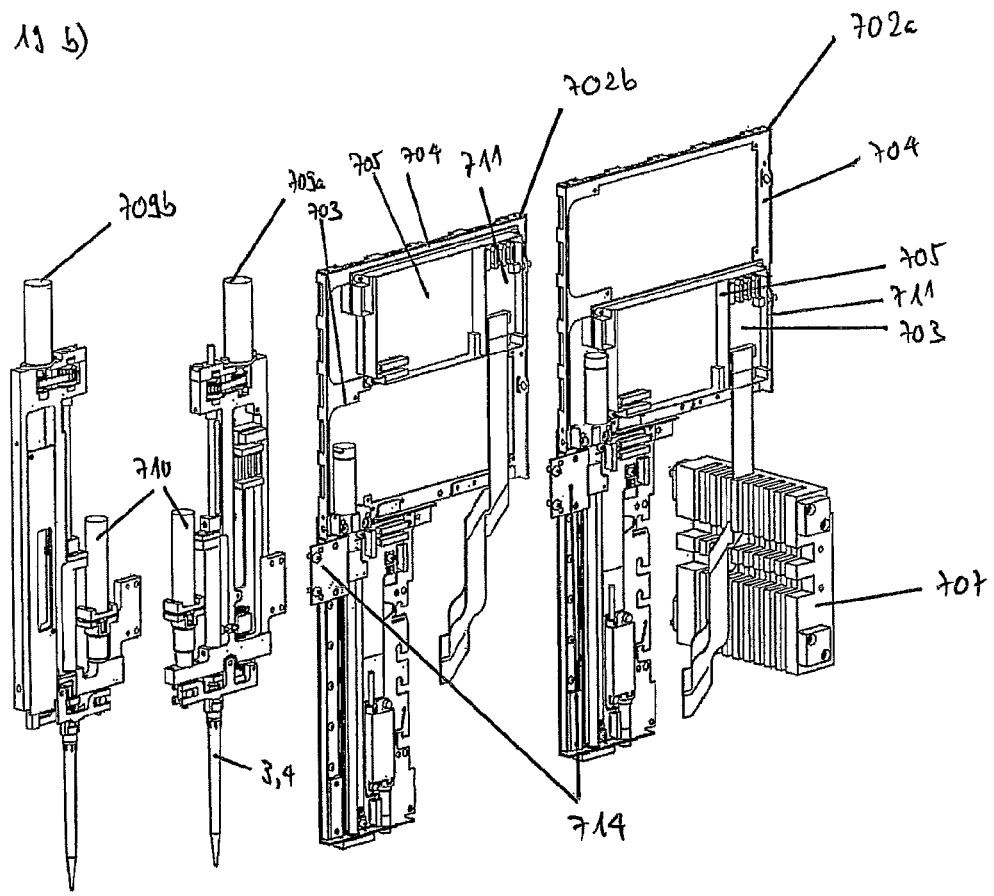

FIG. 19 shows an embodiment of a pipetting device (700) which is only moved in Z-direction. a) Two units (702) are fixed in the support (707). To obtain a sufficiently small raster, e.g. a 9 mm raster, the units (702) are mounted in a staggered manner. Modules (710) on the tools (709) as well as modules (705, 711) on the frame part (703) of the pipette unit (702) are staggered to obtain the required distance between the pipette units (702). B) shows the pipette units (709 a, b) and the frames (702 a, b) in a disassembled manner.

FIG. 20 shows the interface to the frame body (701): a) the frame body is a Y-carriage; the pipetting unit (702) comprises an interacting part (712) which can be engaged with a receiving part (713) of the frame body (701) and releasably fixed. b) shows a detail of the interacting part before engagement. c) shows the frame engaged to the frame body.

Figure 21A:
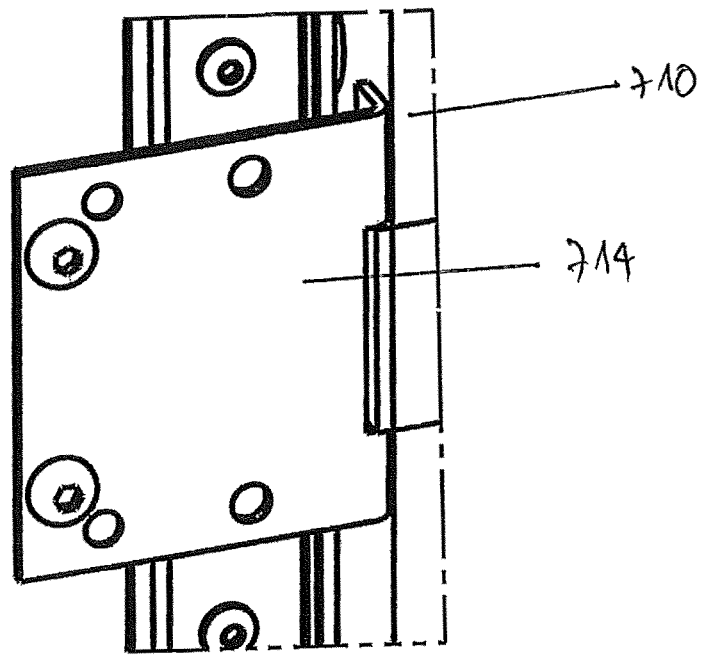
FIG. 21 shows an adapter plate (a) and the adapter plate with pipetting unit fixed to the frame part (b).
Figure 21B:
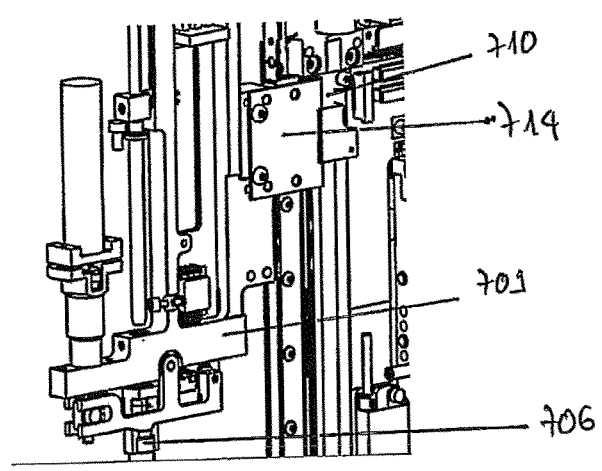

FIG. 21 a) shows an adaptor plate (714) for fixing the pipette tool (709) to the frame part (710) of the pipette unit (702). Other tools (715, 716) may also be attached to said frame part (710). b) shows a detail of the pipette tool (709) fixed to the frame part (702).

The pipette unit may comprise additional modules. Preferably, such modules comprise sensors. Several types of sensors and other modules are shown in FIG. 22 a) to c), e.g., a magnet (720), a hallsensor (721), an init-sensor of the Z-drive (723), an init sensor of the Y-drive (722), an ultrasound sensor (724).

Separation Station

In a preferred embodiment shown in FIG. 24, the separation station (230) comprises at least one fixture (231) comprising at least one magnet (232), preferably a number of magnets equal to a number of vessels (103) in a row (123). Preferably, the separation station (230) comprises a number of fixtures (231) equal to the number of rows (123) of the multiwell plate (101) hereinbefore described. More preferably, six fixtures (231) are mounted on the separation station (230). At least one magnet (232) is mounted on one fixture (231). Preferably, the number of magnets (232) equals the number of vessels (103) in one row (123). Most preferably, eight magnets (232) are mounted on one fixture (231). Preferably, one type of magnet (232) is comprised on said fixture (231). More preferably, the magnet (232) is mounted on one side of the which is oriented towards the vessels with which the magnet interacts.

The fixture (231) is mounted on a base (233). Preferably, said mount is flexible. The base (233) comprises springs (234) mounted thereon. The number of springs (234) is at least one spring per fixture (231) mounted on said base (233). The base further comprises a chamfer (236) which limits the movement of the spring and, consequently, the fixture (231)

comprising the magnets (232). Preferably, any one of said springs (234) is constructed and arranged to interact with a fixture (231). More preferably, said spring (234) is a yoke spring. Said interaction controls the horizontal movement of the fixtures (231). Furthermore, the separation station (230) comprises a frame (235). The base (233) with fixtures (231) is connected to the frame (235) by a moving mechanism as described hereinbefore for the magnets (232) of the first embodiment.

Preferably, said base (233) and fixture (231) is constructed and arranged to move vertically (in Z-direction).

The multiwell plate (101) hereinbefore described is inserted into the separation station (230). The fixture (231) comprising the magnets (232) is moved vertically. Any one fixture (232) is, thus, moved into a space (121) between two rows (123) of vessels (103). The vertical movement brings the magnets (232) mounted on a fixture (231) into contact with the vessels (103). The Z-position is chosen depending on the volume of liquid (215) inside the vessels (103). For large volumes, the magnets (232) contact the vessels (103) in a center position (120) where the vessels (103) are of an almost rectangular shape. For small volumes of liquid (215) where the major part of the liquid (215) is located below the center part (120) of the vessels (103), the magnets (232) preferably contact the conical part (111) of the vessels (103).

A spring is attached to the base (233) of any one frame (231). The spring presses the magnets (232) against the vessels (103). This ensures a contact between magnets (232) and vessels (103) during magnetic separation. Preferably, the magnet (232) contacts the vessel (103) on the side wall (109) located underneath the inlet (105). This has the advantage that liquid which is added by pipetting flows over the sequestered magnetic particles and ensures that particles are resuspended and that all samples in all vessels are treated identically.

This embodiment is particularly suited to separate a liquid (215) comprised in a multiwell plate (101) as hereinbefore described, from magnetic particles (216) when different levels of liquid (215) are contained in the vessels (103) of said multiwell plate (101).

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed:

1. A method for isolating analytes that may be present in fluid samples in an automated system, the method comprising the automated steps of:

a) loading samples on the automated system with identifiers, or identifying loaded samples according to sample type and analytical test to be performed;
    b) transferring instructions from a control unit to a first and a second pipetting device comprising allocation of individual samples to a two-dimensional n×m arrangement of individual tests in a processing plate;
    c) transferring said fluid samples from at least two sample vessels to a at least two vessels of said processing plate with a first pipetting device comprising at least two pipetting units in linear arrangement, wherein said pipetting units are coupled to pipette tips;
    d) combining together a solid support material and said fluid sample in a well of said processing plate for a period of time and under conditions sufficient to permit said analyte to be immobilized on the solid support material;
    e) isolating the solid support material from other material present in the fluid sample in a separation station; and
    f) purifying the analyte in the separation station by separating the fluid sample from the solid support material and washing the materials one or more times with a wash buffer, wherein said solid support material and said washing buffer are mixed by aspirating and dispensing with a second pipetting device, said second pipetting device comprising pipetting units in a two-dimensional n×m arrangement for coupling to pipette tips;

wherein said pipette tips used in step c) are re-used in step f).

2. The method of claim 1, wherein said wells of said processing plate are integrally formed.

3. The method of claim 1, wherein said processing plate is a multiwell plate with a two-dimensional n×m arrangement of vessels.

4. The method of claim 1, wherein said pipette tips are replaced in a tip rack in a two-dimensional n×m arrangement following step c).

5. The method of claim 1, comprising the step of assigning any one pipette tip in said pipette tip rack to a specific vessel of said processing plate with a two-dimensional n×m arrangement of vessels.

6. The method of claim 1, wherein the distance between two adjacent sample vessels is different from the distance between two adjacent vessels of the processing plate, and wherein the distance between two adjacent pipetting units of the first pipetting device is adjustable.

7. The method of claim 1, wherein in step b) instructions are transferred from said control unit to a first processor for transferring samples with said first pipetting device, and instructions are transferred from said control unit to a second processor for the steps carried out by said second pipetting device.

* * * * *